US008656774B2

(12) United States Patent
Moss

(10) Patent No.: US 8,656,774 B2
(45) Date of Patent: Feb. 25, 2014

(54) PHASE SEPARATION DETECTOR FOR FUEL STORAGE TANK

(75) Inventor: Robert A. Moss, Simsbury, CT (US)

(73) Assignee: Veeder-Root Company, Simsbury, CT (US)

( * ) Notice: Subject to any disclaimer, the term of this patent is extended or adjusted under 35 U.S.C. 154(b) by 574 days.

(21) Appl. No.: 12/954,055

(22) Filed: Nov. 24, 2010

(65) Prior Publication Data
US 2011/0185794 A1 Aug. 4, 2011

Related U.S. Application Data

(60) Provisional application No. 61/264,088, filed on Nov. 24, 2009.

(51) Int. Cl.
G01N 9/00 (2006.01)
G01F 23/30 (2006.01)

(52) U.S. Cl.
USPC .................................. 73/440; 73/311; 73/319

(58) Field of Classification Search
USPC ............................................ 73/311, 319, 440
See application file for complete search history.

(56) References Cited

U.S. PATENT DOCUMENTS

| 4,155,254 A | | 5/1979 | Colditz |
| 4,972,710 A | | 11/1990 | Uhlarik et al. |
| 5,347,864 A | * | 9/1994 | Senghaas et al. ............... 73/313 |
| 5,402,110 A | * | 3/1995 | Oliver et al. .................. 340/605 |
| 5,471,873 A | * | 12/1995 | Nyce et al. ....................... 73/453 |
| 5,703,569 A | * | 12/1997 | Oliver et al. .................. 340/605 |
| 5,950,487 A | * | 9/1999 | Maresca et al. ................. 73/293 |
| 7,278,311 B1 | | 10/2007 | Demin |
| 7,343,800 B2 | * | 3/2008 | Harman et al. ................. 73/319 |
| 7,403,860 B2 | | 7/2008 | Hart |
| 7,454,969 B2 | | 11/2008 | Hart |
| 8,286,483 B2 | * | 10/2012 | Mahadevaiah ............. 73/290 R |
| 8,539,828 B2 | * | 9/2013 | Prinstil et al. .................... 73/305 |
| 2006/0169039 A1 | | 8/2006 | Zalenski et al. |
| 2006/0248952 A1 | | 11/2006 | Jarvie |
| 2009/0265132 A1 | | 10/2009 | Schrittenlacher |

FOREIGN PATENT DOCUMENTS

| GB | 937713 A | 9/1963 |
| WO | 2008104967 A2 | 9/2008 |

OTHER PUBLICATIONS

International Search Report and Written Opinion of the International Searching Authority for PCT/US2010/020228, dated Mar. 15, 2010.

* cited by examiner

Primary Examiner — John Fitzgerald
(74) Attorney, Agent, or Firm — Nelson Mullins Riley & Scarborough, LLP

(57) ABSTRACT

A method of determining if phase separation into an upper layer of a first fluid and a lower layer of a first fluid has occurred in a tank containing a first fluid, the method including determining a first density of the first fluid adjacent a top surface of the first fluid, determining a second density of the first fluid adjacent a bottom of the tank, and comparing the first density of the first fluid to the second density of the first fluid to determine if the first fluid has separated into the upper layer of the first fluid and the lower layer of the first fluid separated by a phase separation boundary.

12 Claims, 20 Drawing Sheets

US 8,656,774 B2

PHASE SEPARATION DETECTOR FOR FUEL STORAGE TANK

CLAIM OF PRIORITY

This application claims priority to U.S. Provisional Patent Application Ser. No. 61/264,088, filed Nov. 24, 2009, the entire disclosure of which is incorporated by reference herein.

FIELD OF THE INVENTION

The present invention relates to an apparatus and method used in a fuel storage tank that can be useful for determining whether phase separation has occurred within the fuel storage tank.

BACKGROUND OF THE INVENTION

This application incorporates herein by reference in its entirety the disclosures of U.S. Pat. No. 7,403,860, issued Jul. 22, 2008, and U.S. Published Application No. 2006/0169039, published Aug. 3, 2006.

Fueling environments typically store fuel in large storage tanks located beneath the ground, sometimes referred to as "underground storage tanks" (UST). To comply with environmental laws, rules, and regulations, these storage tanks may be double-walled and equipped with various leak detection sensors and inventory reconciliation systems. One popular leak detection sensor is sold by Veeder-Root Company of 125 Powder Forest Drive, Simsbury, Conn. 06070, the assignee of the present application, under the name "The MAG Plus Inventory Measurement Probe" (MAG PROBE™). This probe is typically matched with a tank monitor, such as the TLS-350R, also sold by Veeder-Root Company. Such probes measure a height of fuel within the storage tank and may optionally measure a height of water (if present). The measurements are reported to the tank monitor for usage by the operator of the fueling environment to evaluate and reconcile fuel inventory and/or detect leaks, as is well understood.

The use of anhydrous ethanol (hereafter "ethanol") as an additive to gasoline is widespread in many countries throughout the world. In particular, 10% ethanol additive (E10) is very popular in the United States. While water separates from plain gasoline, thereby forming a water-fuel interface 34 (FIG. 1), the addition of ethanol allows the fuel, in the instant case E10, to absorb water in a substantially homogenous manner up to approximately 0.4% in suspension, the percentage being dependent on fuel type and temperature. Above 0.4%, the fuel mixture separates into a lower layer 37a and an upper layer 37b (FIGS. 1 and 2), each containing different concentrations of gasoline, ethanol and water. This separation into two distinct layers is referred to as "phase separation". The mixture of lower layer 37a has a higher density and contains larger percentages of ethanol and water than upper layer 37b. Most automobiles are designed to operate with up to 10% ethanol, but the higher percentages of ethanol and water in lower layer 37a can damage E10 rated equipment. A secondary effect is the depletion of ethanol from upper layer 37b which decreases the octane rating of the fuel and can cause poor performance in automobile engines. A tertiary effect is the potential damage to the tank and other associated equipment due to the corrosive mixture of water and ethanol.

Typically, underground storage tanks use a submersible turbine pump (STP) which draws fuel from approximately six (6) inches from the bottom of the tank. If phase separation occurs and the height of the phase separation boundary 37 between lower layer 37a and upper layer 37b is above the STP inlet, automobiles and other equipment can be exposed to non-compliant fuels.

SUMMARY OF THE INVENTION

One aspect of the present invention provides a method of determining if phase separation into an upper layer of a first fluid and a lower layer of a first fluid has occurred in a tank containing a first fluid, the method including determining a first density of the first fluid adjacent a top surface of the first fluid, determining a second density of the first fluid adjacent a bottom of the tank, and comparing the first density of the first fluid to the second density of the first fluid to determine if the first fluid has separated into the upper layer of the first fluid and the lower layer of the first fluid separated by a phase separation boundary.

Another aspect of the present invention provides a fluid level probe for use in a tank containing a first fluid, including a probe shaft which includes a top end and a bottom end; a first float carrying a first magnet, the first float being slidably disposed for movement along the probe shaft and adapted to float at a top surface of the first fluid, a second float carrying a first magnet, the second float being slidably disposed for movement along the probe shaft beneath the first float and adapted to float within the first fluid such that there is magnetic repulsion between the first magnet of the first float and the first magnet of the second float; a frame carrying a first magnet, a third float carrying a first magnet, the third float being slidably disposed for movement along the probe shaft relative to the first magnet of the frame and adapted to float within the first fluid such that there is magnetic repulsion between the first magnet of the third float and the first magnet of the frame, and electronics operative to determine a first distance between the first magnet of the first float and the first magnet of the second float, determine a second distance between the first magnet of the frame and the first magnet of the third float, utilize the first distance to determine a first density of the first fluid adjacent the top surface of the first fluid, utilize the second distance to determine a second density of the first fluid adjacent a bottom of the tank, and determine whether phase separation has occurred within the first fluid by comparing the first density and the second density of the first fluid.

Other objects, features and aspects for the present invention are discussed in greater detail below. The accompanying drawings are incorporated in and constitute a part of this specification, and illustrate one or more embodiments of the invention. These drawings, together with the description, serve to explain the principles of the invention.

BRIEF DESCRIPTION OF THE DRAWINGS

A full and enabling disclosure of the present invention, including the best mode thereof, to one of ordinary skill in the art, is set forth more particularly in the remainder of this specification, including reference to the accompanying drawings, in which.

Figure 1:
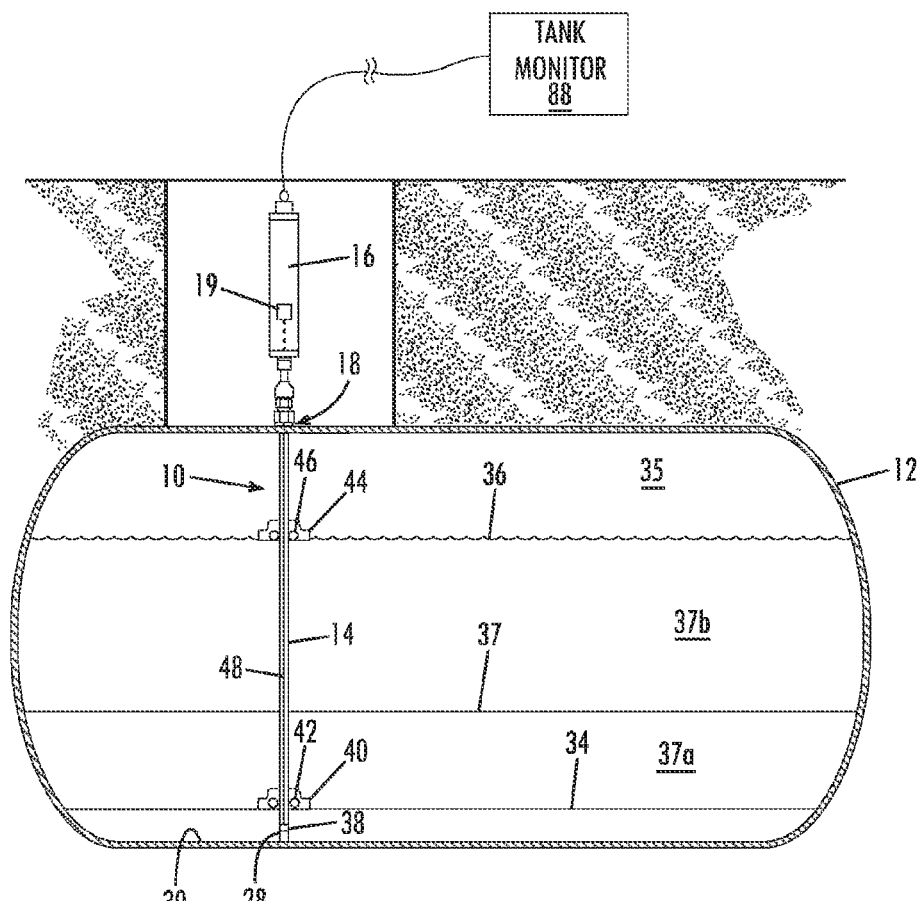
FIG. 1 illustrates a conventional magnetostrictive probe positioned in a fuel storage tank.

Repeat use of reference characters in the present specification and drawings is intended to represent same or analogous features or elements of the invention.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Embodiments of the present invention provide a fuel level probe that measures fuel density as well as fuel height in a fuel storage tank, as well as a method of determining if fuel phase separation has occurred due to the presence of water in the fuel storage tank, as well as the height of the boundary that separates the upper layer from the lower layer. An exemplary fuel level probe comprises a magnetostrictive probe which has a probe shaft inserted into and fixed with respect to the storage tank. The probe has a reference magnet positioned proximate to a terminal end of the probe shaft. A water level float, typically an annular float with a buoyancy between that of water and gasoline, is positioned on the probe shaft and floats at the level of the water-fuel interface. A water level magnet is associated with the water level float so that the level of the water in the fuel storage tank can be ascertained.

A fuel level float, also generally an annular float, is positioned on the probe shaft and floats at the air-fuel interface. A fuel level magnet is associated with the fuel level float so that the level of the fuel in the fuel storage tank can be ascertained. The water level and fuel level floats move freely up and down the probe shaft as the respective levels of fluids (water and fuel) change.

To determine the fuel level and the water level within the fuel storage tank, the probe sends an electric current down a magnetostrictive wire within the probe shaft. The current in the magnetostrictive wire interacts with the magnets and introduces torsional wave reflections in the wire which are detected by a sensor in the probe. The time elapsed between the signal generation and the arrival of the reflections may be used to measure the distance from the sensor to the respective magnet. In accordance with the present invention, the probe is also adapted to determine fuel density. The probe may either perform the calculations to arrive at the density of the fuel or may report its measurements to a tank monitor or other controller so that the controller may perform the calculations to determine the density of the fuel. The density of other fluids may also be measured with the probe of the present invention and the invention is not strictly limited to use in a fueling environment.

A discussion of a conventional magnetostrictive fuel level probe 10 (hereinafter "probe") is first presented herein with reference to FIG. 1. The discussion of preferred embodiments of the present invention follows beginning with reference to FIG. 2 below.

Thus, referring now to FIG. 1, the probe 10 is a magnetostrictive probe, such as the MAG PROBE™ magnetostrictive probe sold by the assignee of the present invention, namely Veeder-Root Company of 125 Powder Forest Drive, Simsbury, Conn. 06070. The probe 10 is positioned partially in a fuel storage tank 12. Specifically, the probe includes a probe shaft 14 that extends into the fuel storage tank 12 while a canister 16 is positioned outside of fuel storage tank 12. As shown, canister 16 is attached to probe shaft 14 via fittings 18. However, fittings may or may not be used depending on the application. Canister 16 includes electronics 19 which enable operation of the probe 10, as further explained below.

In use, most fuel storage tanks, such as fuel storage tank 12, have a small amount of water therein. For pure gasoline without additives (such as ethanol), this water collects at the bottom of fuel storage tank 12, forming a water-fuel interface 34. The fuel sits on top of the water and has an air-fuel interface 36 at ullage 35 of fuel storage tank 12. Probe shaft 14 extends through both interfaces 34 and 36.

Figure 2:
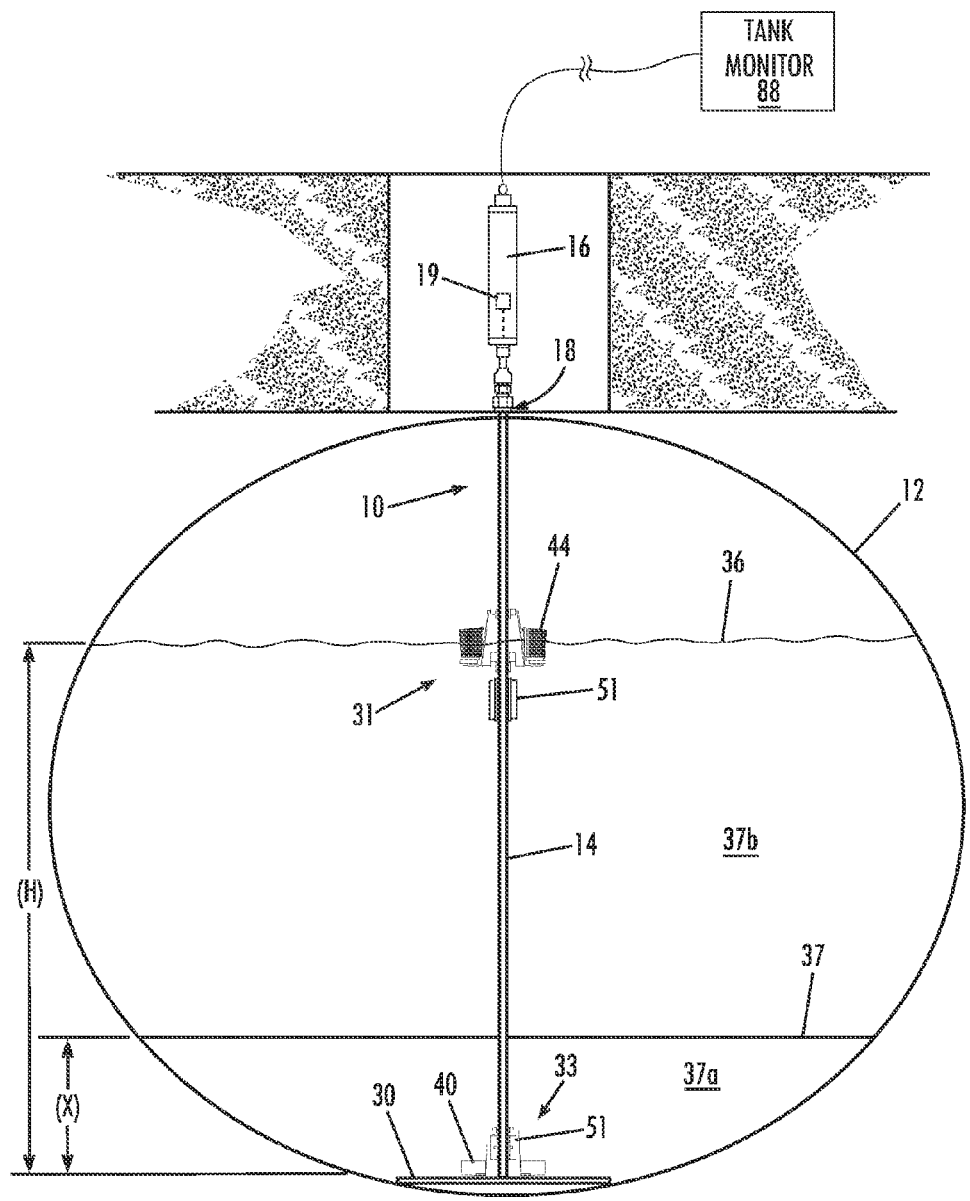
FIG. 2 illustrates a magnetostrictive probe system utilizing a pair of magnetostrictive density detectors according to the first embodiment of the present invention.

Probe shaft 14 has a reference magnet 38 positioned proximate a terminal end 28 of probe shaft 14 at a fixed, known distance from terminal end 28. Reference magnet 38 may be positioned internal to probe shaft 14, or externally in a boot (not shown) that slips over the terminal end of probe shaft 14. A water level float 40, typically an annular float, is positioned on probe shaft 14 and floats at the level of water-fuel interface 34. A water level magnet 42 is associated with water level float 40 so that the level of the water in fuel storage tank 12 can be ascertained. As previously noted, for fuel storage tanks 12 containing fuel to which anhydrous ethanol, alcohol, etc., have been added, water layer 34 may not form because the water is absorbed by the fuel, as shown in FIG. 2.

A fuel level float 44, also generally an annular float, is positioned on the probe shaft 14 and floats at air-fuel interface 36. A fuel level magnet 46 is associated with fuel level float 44 so that the level of the fuel in fuel storage tank 12 can be ascertained. It should be appreciated that floats 40 and 44 move freely up and down probe shaft 14 as the respective levels of fluids (water and fuel) change. Likewise, the buoyancy of floats 40 and 44 is determined by the fluid on which they will be floating. Such parameters are conventional and well understood by someone of ordinary skill in the art. However, the interested reader is directed to the MAG PLUS PROBE ASSEMBLY GUIDE, published by Veeder-Root, which is available online at http://www.veeder.com/page/search.html?keywords=mag+probe. The ASSEMBLY GUIDE is hereby incorporated by reference in its entirety.

To determine the fuel level and the water level within fuel storage tank 12, probe 10 generates an electric current with a current source within electronics 19 positioned in canister 16 and sends the electric current down a magnetostrictive wire 48 in probe shaft 14. Then, probe 10 detects torsional wave reflections induced by magnets 42 and 46 of floats 40 and 44, respectively, and reference magnet 38. The torsional wave reflections are detected with a detector such as a sensing coil (not shown explicitly) of electronics 19.

The first reflection to arrive at the detector is a reflection from fuel level magnet 46 which is associated with fuel level float 44. The second reflection to arrive at the detector is a reflection from water level magnet 42 which is associated with water level float 40. A third reflection arrives from reference magnet 38. Since the speed of the torsional wave in the magnetostrictive wire 48 is known (typically about 3000 m/s), it is possible to calculate the distance between the detector and the magnet that induced the torsional wave. The detector thus measures the time elapsed between the origination of the pulse and the arrival of each torsional wave reflection. If the distance from the detector to a particular magnet is known, it is a well known exercise to determine the level of that particular magnet within fuel storage tank 12.

Alternatively, the difference in arrival times of torsional waves is used to measure the distance between the level magnets and reference magnet 38. That is, the distance from bottom 30 to reference magnet 38 (the height of the reference magnet) is known. By measuring the time difference between the arrival of torsional waves from, for example, water level magnet 42 and reference magnet 38, the distance between the two magnets 38 and 42 may be determined. Specifically, the velocity of the torsional wave is multiplied by the time, and a distance is generated. This distance is added to the height of the reference magnet and from this calculation, the height of water level magnet 42 is determined. Similar calculations may be made for fuel level magnet 46. Put another way, the heights of the magnets relative to bottom 30 of fuel storage tank 12 are determinable.

Probe 10 reports the measured reflections to a tank monitor 88, such as the TLS-350R manufactured and sold by Veeder-Root Company. Tank monitor 88 uses the data from probe 10, and specifically, the measured reflections to determine the level and thus, the volume of fuel, within fuel storage tank 12.

For example, tank monitor 88 may determine a volume of fuel within fuel storage tank 12 from the height of the fuel level, as determined by the height of fuel level float 44 (and as measured by the first reflection or its relationship to the reflection of reference magnet 38). From this height, a conventional tank strapping algorithm or other conventional technique may be applied, as is well understood in the art, to convert the fuel level to arrive at the volume of fuel within fuel storage tank 12. For more information on the operation of a magnetostrictive fuel level probe, the interested reader is referred to U.S. Pat. No. 5,076,100, which is hereby incorporated by reference in its entirety.

Figure 3:
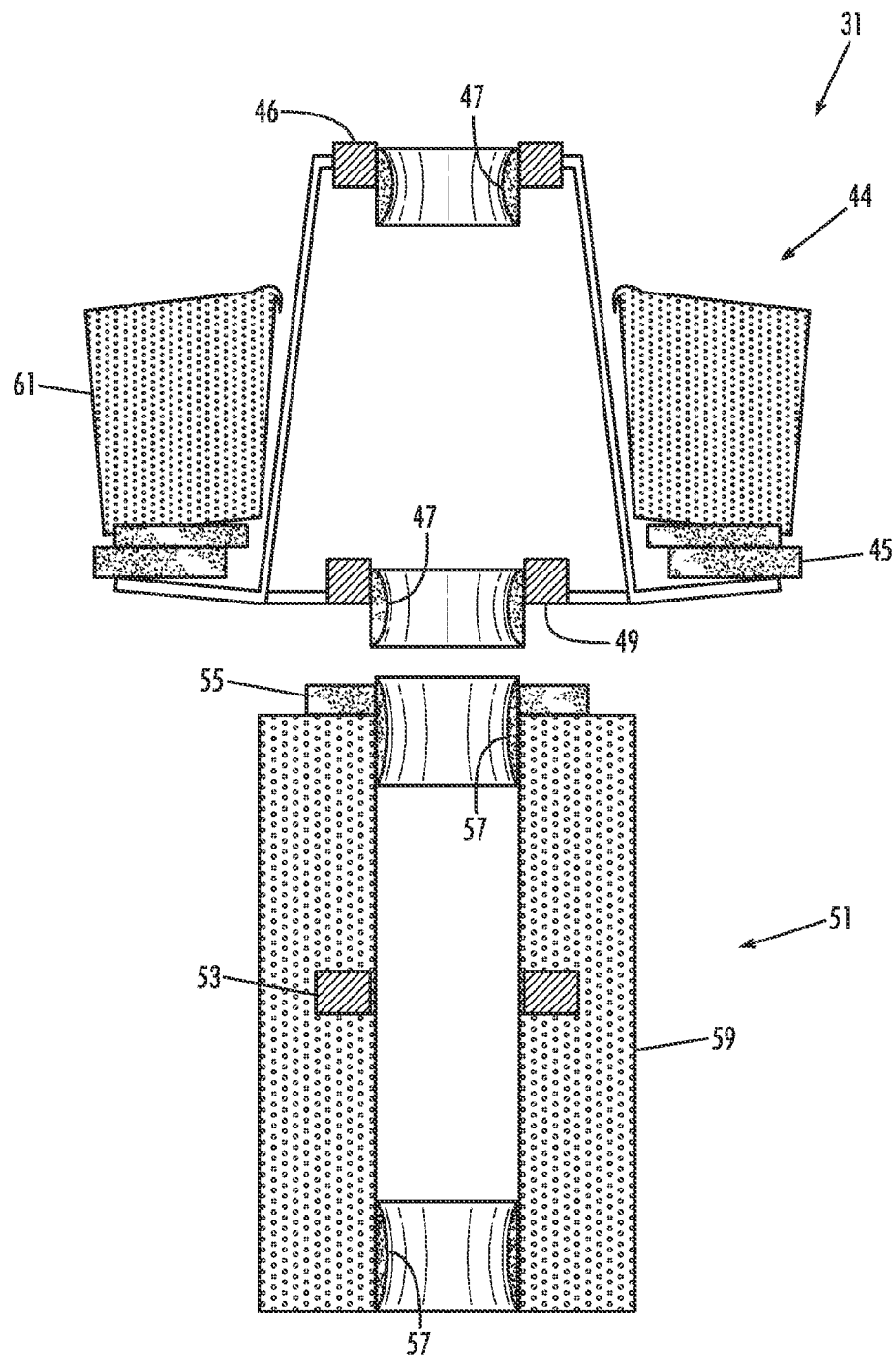
FIG. 3 illustrates the surface layer magnetostrictive density detector used in the system of FIG. 2.
Figure 4:
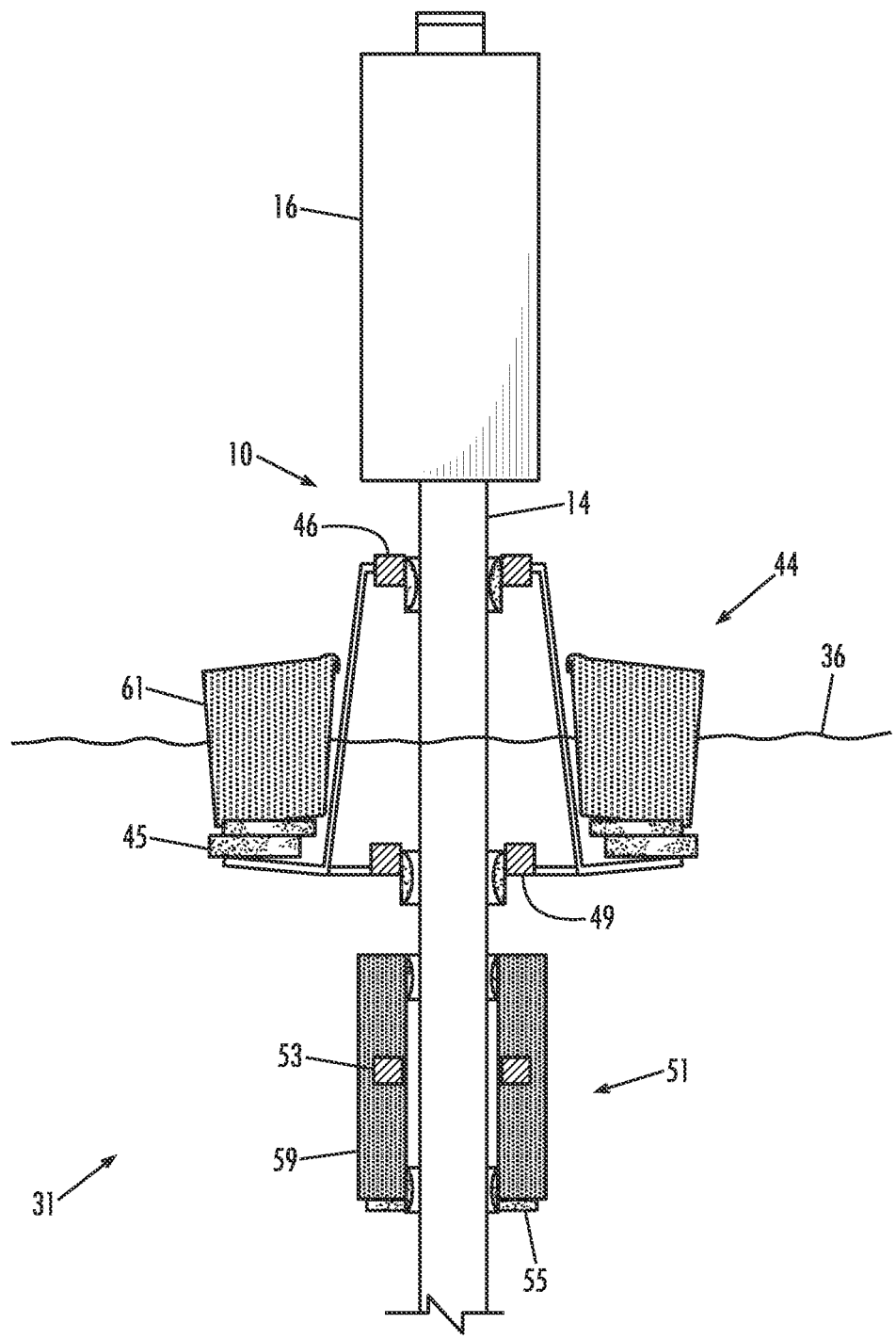
FIG. 4 illustrates the surface layer magnetostrictive density detector of FIG. 3 positioned on a probe shaft.

Referring now to FIGS. 2 through 4, a magnetostrictive density detector 31 for determining fuel density at the surface layer of the fuel is shown. Magnetostrictive density detector 31 includes a fuel level float 44 and density float 51, and may be used in combination with magnetostrictive probe 10 such as shown in FIG. 1. Fuel level float 44 includes ballast 45, a fuel level magnet 46, balancing lips 47, a repulsion magnet 49 and a body 61. In the embodiment shown, repulsion magnet 49 is added to fuel level float 44 of an existing magnetostrictive probe 10, such as previously discussed. Repulsion magnet 49 is provided in the shown embodiment because fuel level magnet 46 is positioned on an upper portion of fuel level float 44, thereby limiting its ability to interact with density float 51, as discussed in greater detail below. Balancing lips 47 ensure that fuel level float 44 is free to move vertically along probe shaft 14 as fuel level 36 within fuel storage tank 12 changes.

Density float 51 includes a density magnet 53, balancing lips 57, ballast 55 and a body 59. Density magnet 53 is positioned on density float 51 such that adequate magnetic repulsion forces are present between repulsion magnet 49 of fuel level float 44 and density magnet 53 of density float 51. Similarly to balancing lips 47 of fuel level float 44, balancing lips 57 ensure that density float 51 is free to move along probe shaft 14 as fuel level 36 and the density of the fuel change. Also similar to fuel level float 44, ballast 55 is provided and may be changed such that the buoyancy of density float 51 may be adjusted as necessary, as determined by the fluid in which it will be floating.

Figure 5:
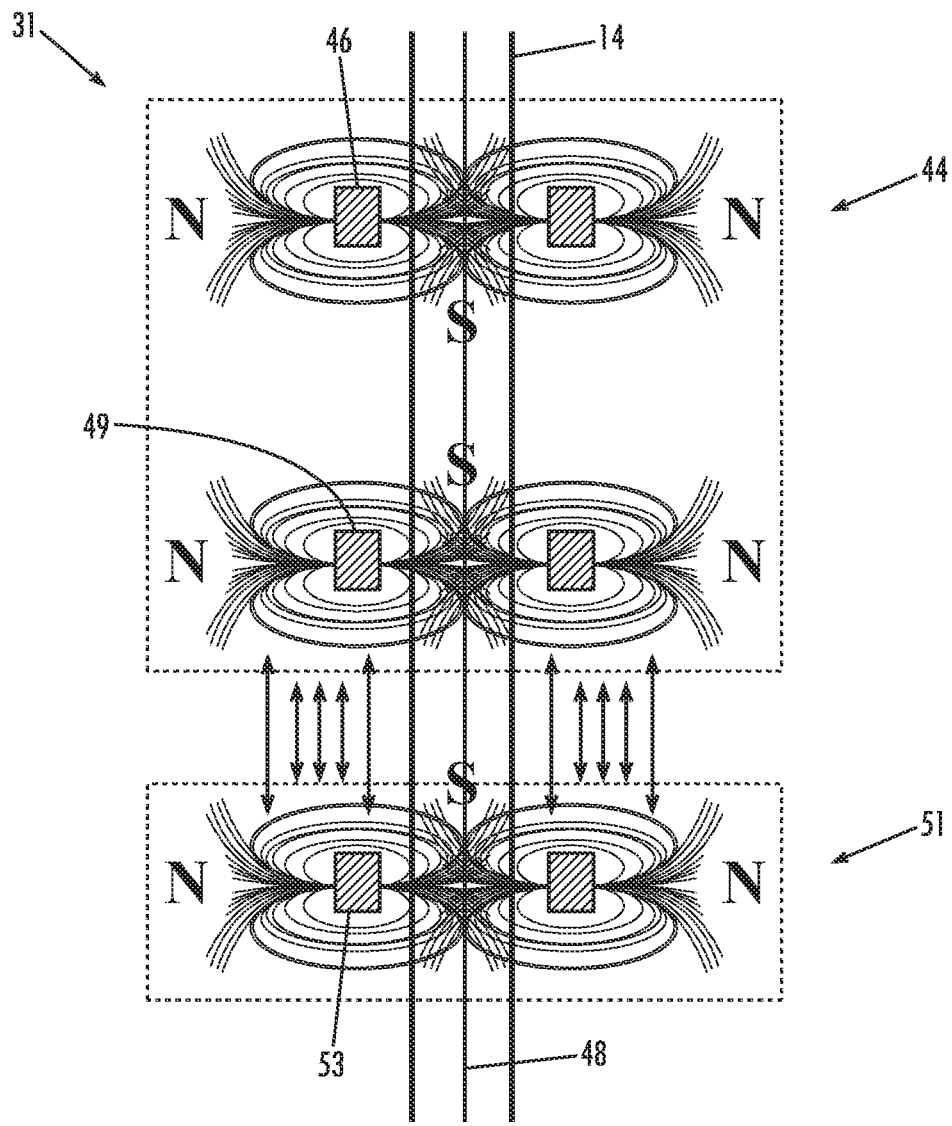
FIG. 5 is a schematic of the magnetostrictive density detector of FIG. 3, illustrating the principle of magnetic repulsion found in the detector.

Referring additionally to FIG. 5, the determination of fuel density by magnetostrictive density detector 31 is based on the effects of magnetic repulsion forces between repulsion magnet 49 positioned on fuel level float 44 and density magnet 53 positioned on density float 51. In short, magnetic repulsion forces generated between repulsion magnet 49 and density magnet 53 will affect the position of density float 51 relative to fuel level float 44, or more specifically, the position of density magnet 53 relative to repulsion magnet 49 along magnetostrictive wire 48 of probe shaft 14.

For the surface layer magnetostrictive density detector 31, density float 51 is calibrated such that it is less buoyant than fuel level float 44 in the fluids for which the detection of density changes is desired. As well, density float 51 is preferably less massive than fuel level float 44 such that the position of density float 51 along probe shaft 14 will change as the fuel density changes but the position of fuel level float 44 will be relatively unaffected. As such, fuel level float 44 and density float 51 are designed such that density float 51 is most affected by the magnetic repulsion forces that exist between repulsion magnet 49 and density magnet 53. Note, however, that density magnet 53 of density float 51 exerts an upward force on fuel level float 44. As such, it may be necessary to adjust the amount of ballast 45 on fuel level float 44 in order to maintain the desired amount of buoyancy and, therefore, accurate fuel level measurement by fuel level magnet 46.

As is known, the vertical position of a float disposed within a fluid will be altered as the density of the fluid changes. For example, as the density of the fluid increases, the float will rise, and as the density decreases, the float will move lower in the fluid. As such, when fuel level float 44 and density float 51 are placed in fuel, the less-massive density float 51 will be repelled by fuel level float 44 due to magnetic repulsion forces between repulsion magnet 49 and density magnet 53, and density float 51 will be made to sink deeper into the fuel as the fuel density decreases. Density magnet 53 will move lower in the fuel along probe shaft 14 until the repulsion forces between the magnets can no longer overcome the buoyant force exerted on density float 51 by the fuel. When the opposing forces null and density float 51 reaches equilibrium, it levitates at a constant position relative to probe shaft 14 and, therefore, magnetostrictive wire 48. The distance at which repulsion magnet 49 and density magnet 53 are separated when at equilibrium in a fluid of known density is a log function of the magnetic repulsion forces. As such, using the previously discussed magnetostrictive probe 10 as shown in FIG. 1, the separation distance between repulsion magnet 49 and density magnet 53 can be determined and a formula derived to determine the fuel density at the surface of the fuel.

Figure 6:
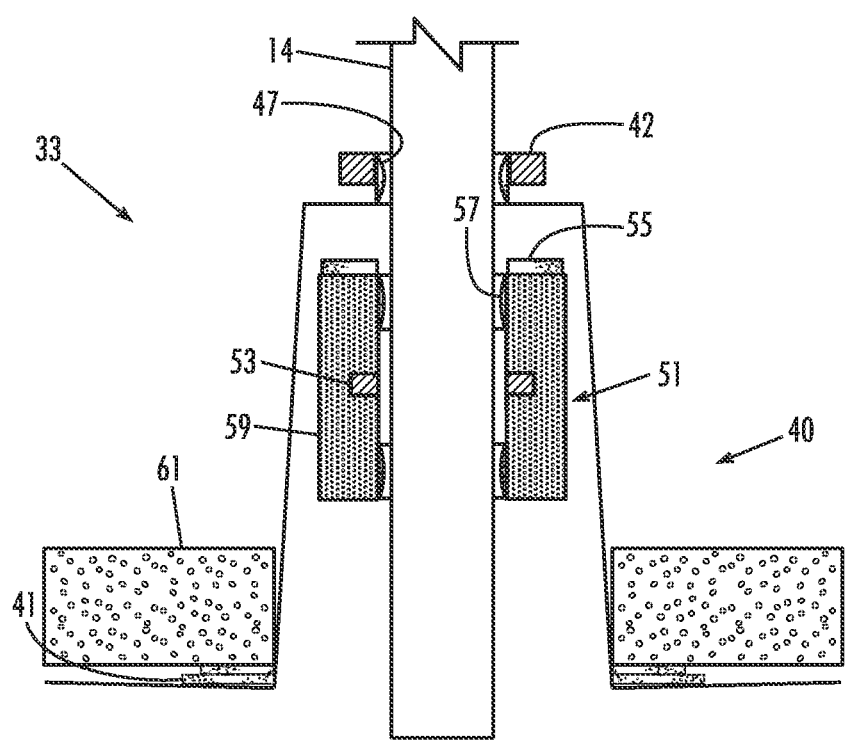
FIG. 6 illustrates the bottom layer magnetostrictive density detector of FIG. 3.

Referring now to FIG. 6, a magnetostrictive density detector 33 for determining fuel density at the bottom of fuel storage tank 12 is shown. As previously discussed, a water layer may or may not be present at the bottom of the storage tank depending upon whether or not the stored fuel includes ethanol. In FIG. 2, the stored fuel includes ethanol and enough water has been absorbed to cause the fuel to undergo phase separation. As such, there is no water layer present and lower layer 37a and upper layer 37b meet at phase separation boundary 37.

Magnetostrictive density detector 33 includes a water level float 40 and a density float 51, and is used in combination with magnetostrictive probe 10 shown in FIG. 1. Water level float 40 includes ballast 41, a water level magnet 42, balancing lips 47 and a body 61. Balancing lips 47 ensure that water level float 40 is free to move along probe shaft 14 as the water-fuel interface 34, if there is one, within the tank changes. As noted, the fuel contained in fuel storage tank 12 includes ethanol. As such, any water present in fuel storage tank 12 below the saturation level will eventually be absorbed into the fuel rather than forming a water layer, and water level float 40 therefore rests on bottom 30 of fuel storage tank 12. However, if fuel that does not contain ethanol is stored at some point in fuel storage tank 12, water level float 40 will once again allow for the detection of the formation of a water later should that occur.

Density float 51 includes a density magnet 53, balancing lips 57, ballast 55 and a body 59. Density magnet 53 is positioned on density float 51 such that adequate magnetic repulsion forces are present between water level magnet 42 of water level float 40 and density magnet 53 of density float 51. Similarly to balancing lips 47 of water level float 40, balancing lips 57 ensure that density float 51 is free to move along probe shaft 14 as water-fuel interface 34 and the density of the fuel change. Also similar to water level float 40, ballast 55 is provided and may be changed such that the buoyancy of density float 51 may be adjusted as necessary as determined by the fluid in which it will be floating.

Figure 7:
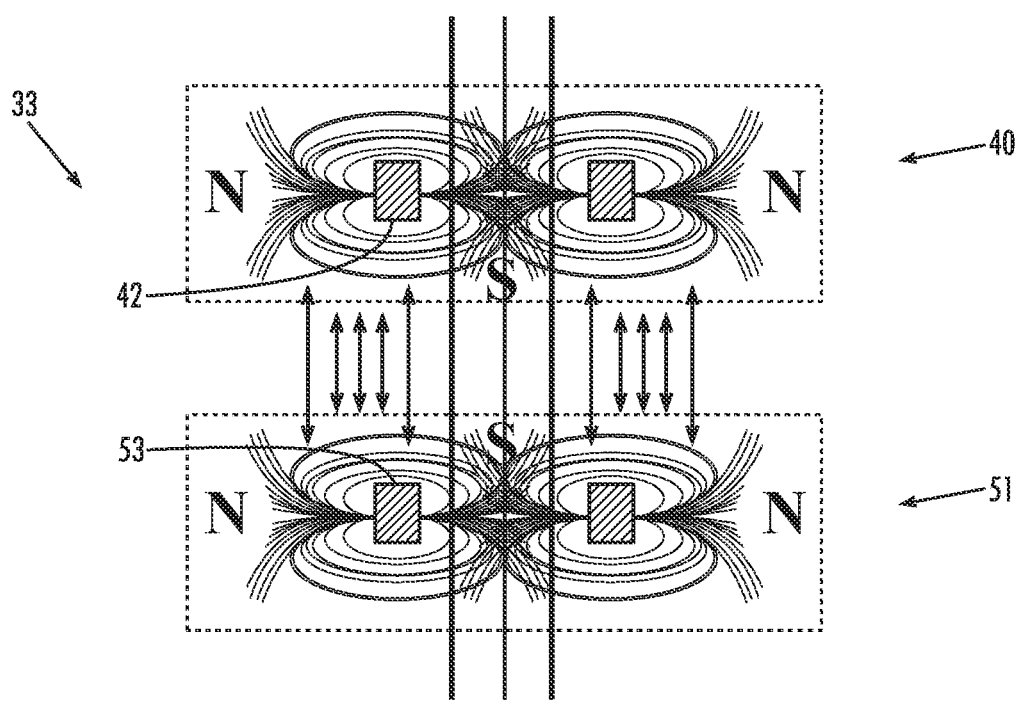
FIG. 7 is a schematic of the bottom layer magnetostrictive density detector of FIG. 3, illustrating the principle of magnetic repulsion found in the detector.

Referring additionally to FIG. 7, the determination of fuel density by magnetostrictive density detector 33 is based on the effects of magnetic repulsion forces between water level magnet 42 (also functioning as a repulsion magnet) positioned on water level float 40 and density magnet 53 positioned on density float 51. In short, magnetic repulsion forces between water level magnet 42 and density magnet 53 will affect the position of density float 51 relative to water level float 40, or more specifically, the position of density magnet 53 relative to water level magnet 42 along magnetostrictive wire 48 of probe shaft 14.

For water layer magnetostrictive density detector 33, density float 51 is calibrated such that it is less buoyant than water level float 40 in the fluids for which the detection of density changes is desired. As well, density float 51 is preferably less massive than water level float 40 such that the position of density float 51 along probe shaft 14 will change as fuel density changes but the position of water level float 40 will be relatively unaffected. As such, water level float 40 and density float 51 are designed such that density float 51 is most affected by the magnetic repulsion forces that exist between water level magnet 42 and density magnet 53. Note, however, that density magnet 53 of density float 51 will be exerting an upward force on water level float 40. As such, it may be necessary to adjust the amount of ballast 41 on water level float 40 in order to maintain the desired amount of buoyancy and, therefore, accurate water level measurement by water level magnet 42.

As is known, the vertical position of a float disposed within a fluid will be altered as the density of the fluid changes. For example, as the density of the fluid increases, the float will rise, and as the density decreases, the float will move lower in the fluid. As such, when water level float 40 and density float 51 are placed in fuel, the less-massive density float 51 will be repelled by water level float 40 due to magnetic repulsion forces between water level magnet 42 and density magnet 53, and density float 51 will be made to sink deeper into the fuel as the fuel density decreases. Density magnet 53 will move lower in the fuel along probe shaft 14 until the repulsion forces between the magnets can no longer overcome the buoyant force exerted on density float 51 by the fuel. When the opposing forces null and density float 51 reaches equilibrium, it levitates at a constant position relative to probe shaft 14 and, therefore, magnetostrictive wire 48. The distance at which water level magnet 42 and density magnet 53 are separated when at equilibrium in a fluid of known density is a log function of the magnetic repulsion forces. As such, using the previously discussed magnetostrictive probe 10 as shown in FIG. 1, the separation distance between water level magnet 42 and density magnet 53 can be determined and a formula derived to determine the fuel density at the surface of the fuel.

Referring again to FIG. 2, a method of determining whether or not phase separation has occurred in fuel storage tank 12, as well as determining the height of phase separation boundary 37, is discussed. In the present example, fuel storage tank 12 contains E10 fuel. When enough water enters fuel storage tank 12 to cause phase separation of the fuel, lower layer 37a and upper layer 37b are formed and are separated at phase separation boundary 37. Boundary layers of phase separated fuels are disturbed and mixed by events such as tank filling. When fuel storage tank 12 is refilled, the new and old fuels are in the mixed state and the densities measured by magnetostrictive density detectors 31 and 33, as previously described when discussing FIGS. 3 through 5 and FIGS. 6 and 7, respectively, will be approximately equal. This initial uniform density can be used to determine the average density of the fuel.

If there is sufficient water in the fuel mixture, phase separation will occur. For a known concentration of ethanol to gasoline, there are distinct densities for upper and lower layers 37b and 37a for a given concentration of water above the saturation point, and also a distinct volume ratio (VR) between the two phases. Because the overall fuel height (H) is known from fuel level float 44, the volume of the phase separated lower layer 37a can be determined from the two density readings. The height (X) of phase separation boundary 37 can also be determined using a conventional tank strapping algorithm or a tank chart, as is understood in the art. A warning can be given to avoid dispensing improper ethanol concentrations by estimating when the height (X) of phase separation boundary 37 is approaching the level of the STP intake.

To determine whether phase separation has occurred, and if so, the height (X) of phase separation boundary layer 37, magnetostrictive density detector 33 is used to measure the fuel density ($\rho_B$) at the bottom of fuel storage tank 12, and magnetostrictive density detector 31 is used to measure the fuel density ($\rho_T$) at the top of fuel storage tank 12 as well as total volume of fuel ($V_{Tot}$). If the initial difference between ($\rho_B$) and ($\rho_T$) is less than some limit ($\Delta\rho_L$), then the volumes of upper layer 37b and lower layer 37a caused by phase separation can be determined by: If $\Delta\rho=\rho_T-\rho_B<\Delta\rho_L$ Initially, then set $$\rho_{init} = \frac{\rho_T + \rho_B}{2}$$

As the difference in the densities begins to increase, the measurements are related by: $\rho_{init}V_{Tot}=\rho_B V_B+\rho_T V_T$ where $V_T=V_{Tot}-V_B$ so $$\rho_{init}V_{Tot} = \rho_B V_B + \rho_T(V_{Tot} - V_B)$$

$$V_B = \frac{V_{Tot}(\rho_{init} - \rho_T)}{\rho_B - \rho_T}$$

Having determined the volume ($V_B$) of the phase separated lower layer 37a allows the height (X) of phase separation boundary 37 to be determined since the height of lower layer 37a is a function of its volume ($V_B$) and the configuration of the bottom of fuel storage tank 12. As such, a tank chart or tank strapping algorithm can now be used to determine the height (X) of phase system boundary layer 37, as is known in the art. This technique is theoretically sound, but in application the upper density does not change significantly.

Note, although the current embodiment addresses using the disclosed magnetostrictive density detectors to measure the densities of the fuel at the top and the bottom of the fuel storage tank in order to determine whether or not phase separation has occurred, alternate methods of determining the densities are encompassed by the present invention. For example, the densities can be determined by measuring various properties of the fuel such as its capacitance, inductance, etc. As well, the ultrasonic properties of the fuel at its various levels can be measured in order to determine the composition of the fuel, and therefore its densities at the various levels. Any known methods of determining the density of the fuel at the desired levels are encompassed within the present invention.

Figure 8:
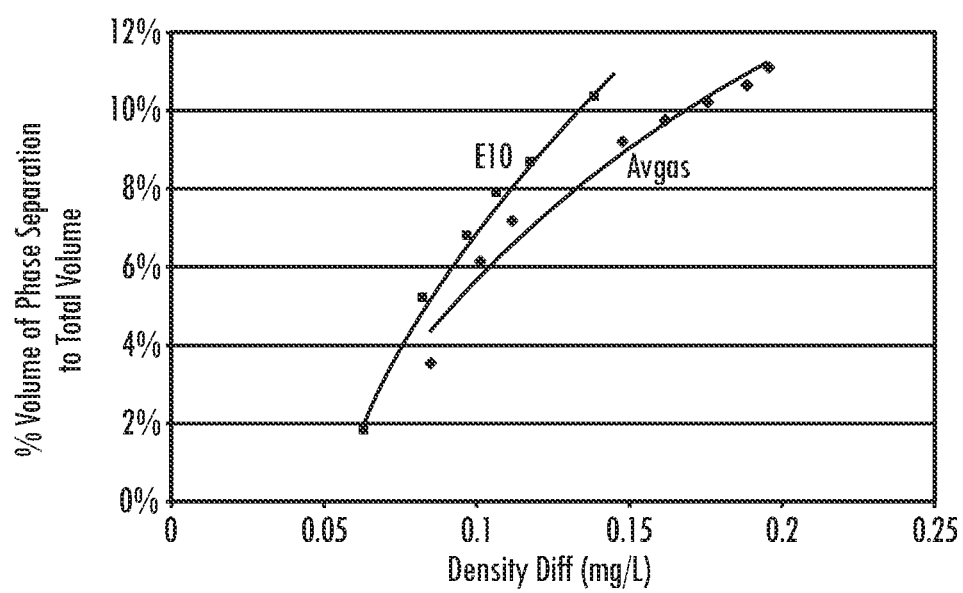
FIG. 8 is a graph illustrating an empirical method of determining the height of a phase separation boundary layer, in accordance with an alternate embodiment of the present invention.

An alternate method of the present invention is an empirical method that is based on the density difference between upper layer 37b and lower layer 37a of the phase separation, which is well within the measurement range of typical density detectors. Referring now to FIG. 8, the graph shows actual measurements for differences between the densities of upper layer 37b and lower layer 37a for both Aviation Gasoline (Avgas) with 10% ethanol added (density=0.700 gm/L) and standard E10 fuel (density=0.750 gm/L). The (x) axis is the difference in density between upper and lower layers 37b and 37a and the (y) axis is the percent volume of the lower phase separation layer over the total volume ($V_{Tot}$) of fuel in the tank. Once the difference in density between upper and lower layers 37b and 37a is determined, one enters the graph along the (x) axis to determine the percent volume of lower layer 37a over the total volume ($V_{Tot}$) of fuel in fuel storage tank 12, which is determined by magnetostrictive density detector 31. This allows the volume ($V_B$) of the phase separated lower layer 37a to be determined by a single ratio. Having determined the volume ($V_B$) of the phase separated lower layer 37a allows the height (X) of phase separation boundary 37 to be determined since the height of lower layer 37a is a function of its volume ($V_B$) and the configuration of the bottom of fuel storage tank 12. As such, a tank chart or tank strapping algorithm can now be used to determine the height (X) of phase system boundary layer 37, as is known in the art. The curves are differentiated by the density of the upper layer, which is nearly constant before and after phase separation. A multitude of such curves can be generated for different density fuels.

Both methods outlined above typically contemplates complete mixing of the water and fuel to effectively measure the volume of the phase separation layer. With complete mixing, water below the saturation level (0.4% water for E10) will dissolve into the E10 mixture. Water levels above the saturation point will cause two stable layers containing different concentrations of ethanol, gasoline and water. However, when only limited mixing occurs, water amounts below the saturation level for a given ethanol blend can form a quasi-stable state which can be referred to as local phase separation. This state contains a second lower layer with concentrations of water, ethanol and gasoline that change over time or with varying levels of mixing. The next embodiment thus describes a method for measuring a boundary layer volume when local phase separation has occurred.

Figure 9:
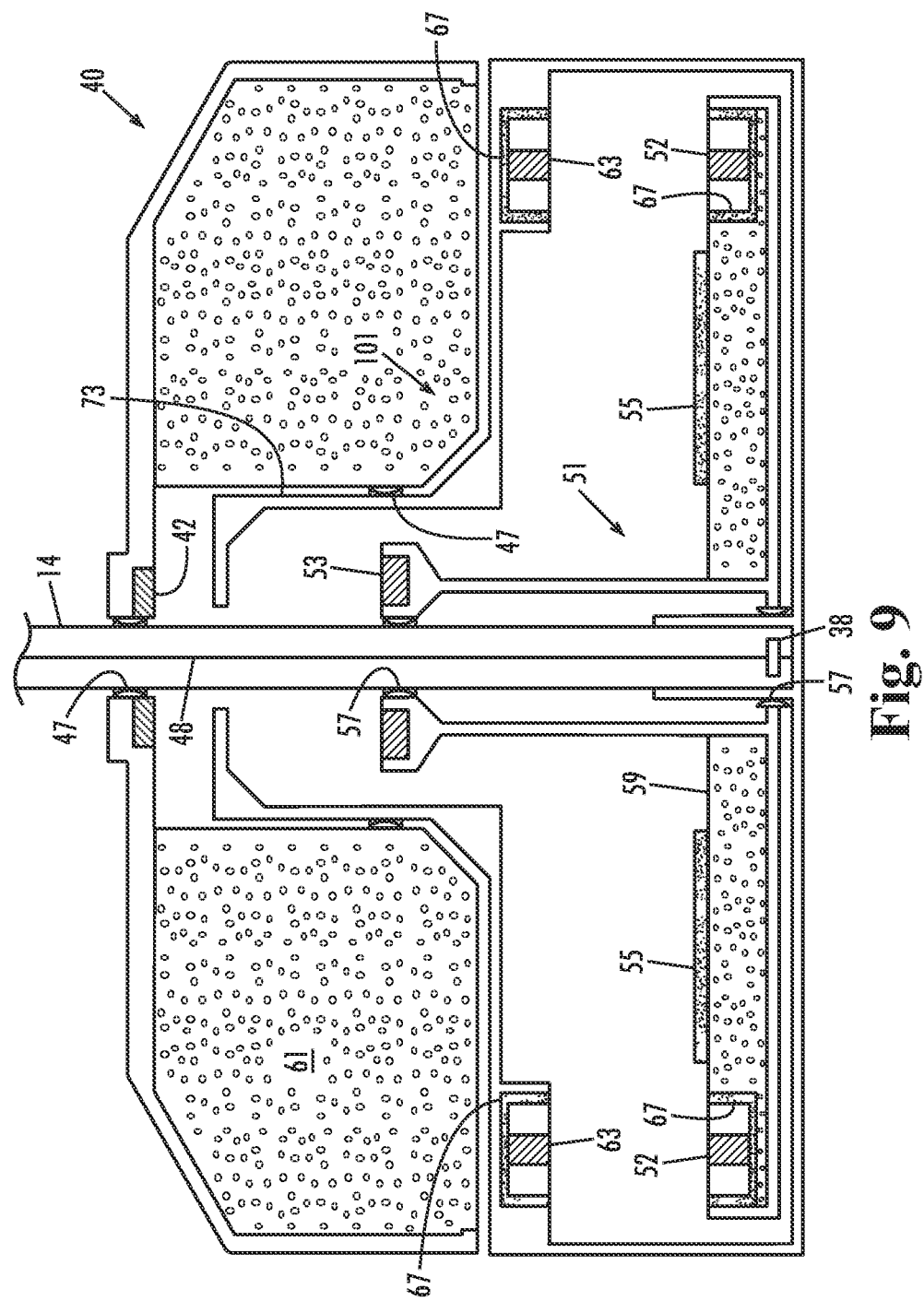
FIG. 9 is a second embodiment of a bottom layer magnetostrictive density detector in accordance with the present invention.

A preferred embodiment of magnetostrictive density detector 101 for measuring a boundary layer volume during local phase separation includes a water level float 40 above a lower density float 51, as shown in FIG. 9. When local phase separation occurs, the density difference between the upper and lower density floats indicates a potential phase separation issue. If this local phase separation boundary height becomes large and dense enough to lift water level float 40, the precise depth of the local boundary layer can be determined because the upper layer density and lower layer density are known. These densities, in conjunction with the buoyancy characteristics of water level float 40 can be used to determine the precise depth of the local phase separation boundary layer and, by way of the tank chart, the volume. Prior to lifting the water float, the difference between the upper density float and the lower density float within the water float can be used to indicate that the phase separation boundary has reached the level of the lower density float.

As shown in FIG. 9, magnetostrictive density detector 101 is used in combination with the magnetostrictive probe shown in FIG. 1. Water level float 40 includes a water level magnet 42, balancing lips 47 and a body 61. Balancing lips 47 ensure that water level float 40 is free to move along probe shaft 14 as the level of any water, or local phase separation boundary layer as discussed above, within the tank changes. Density float 51 includes a density magnet 53, balancing lips 57, ballast 55, a body 59 and a repulsion magnet 52. Repulsion magnet 52 is positioned on density float 51 such that adequate magnetic repulsion forces are present between repulsion magnet 52 and repulsion magnet 63 that is received on a boot 73 that is slidably received over the bottom end of probe shaft 14. Repulsion magnet 63 and repulsion magnet 52 are each disposed within a U-shaped pole piece 67 on boot 73 and density float 51, respectively. The purpose of U-shaped pole pieces 67 is to concentrate the magnetic fields of repulsion magnets 52 and 63, thereby maximizing the repulsive forces between them and allowing magnetostrictive density detector 101 to cover a wide range of densities. As well, U-shaped pole pieces 67 help minimize interaction of repulsion magnets 52 and 63 with both magnetostrictive wire 48 and the bottom of the fuel tank, which could otherwise interfere with the desired torsional waves in magnetostrictive wire 48 or cause density float 51 to be attracted to the bottom of the fuel tank, respectively. In contrast, density magnet 53 is disposed on density float 51 so as to be in close proximity to probe shaft 14. Note, as compared to previously discussed embodiments, body 59 of density float 51 is configured in a very thin, flat, pancake-like configuration so that density float 51 can respond to a very thin layer of water-ethanol mix on the bottom of the fuel tank, as may occur with local phase separation boundary layers.

Figure 10:
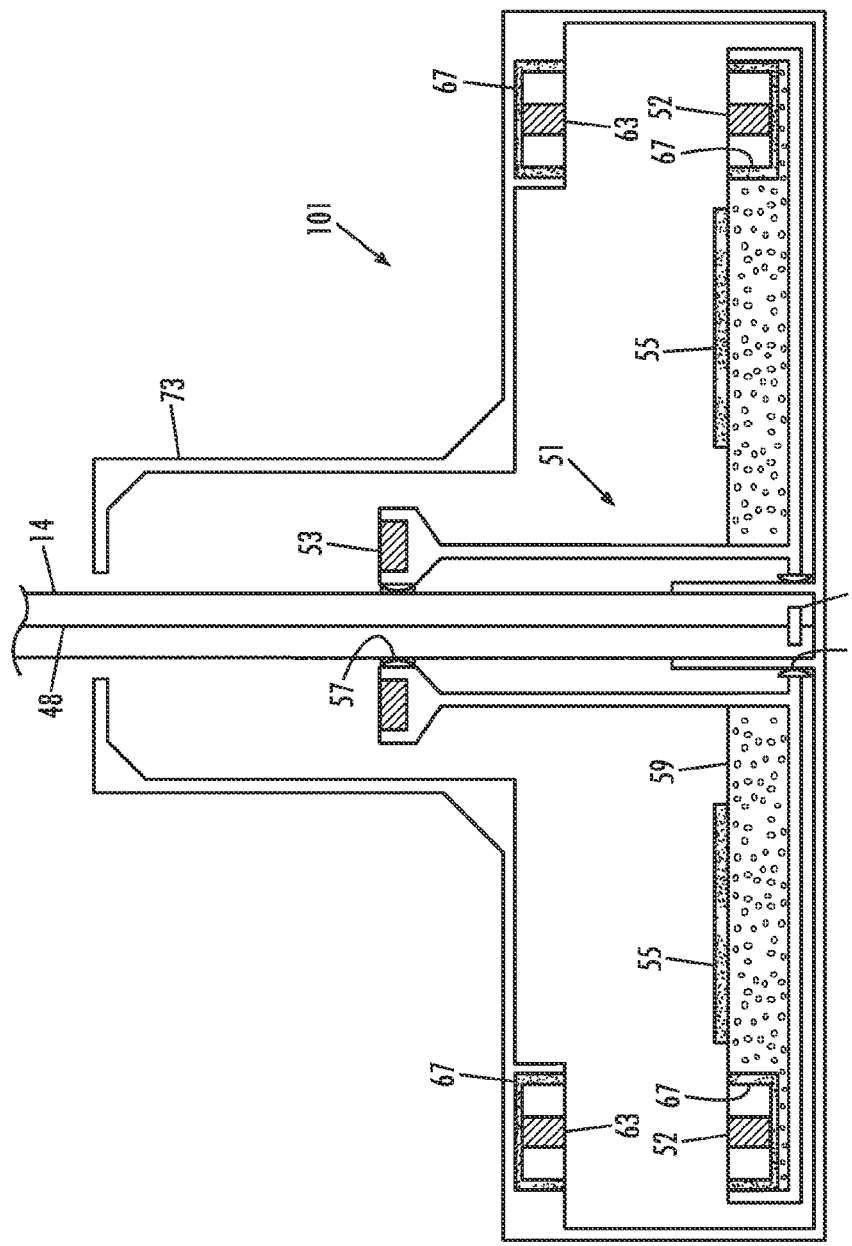
FIG. 10 is a third embodiment of a bottom layer magnetostrictive density detector in accordance with the present invention.

Referring now to FIG. 10, an alternate embodiment of a magnetostrictive density detector 101 for detecting fuel density at the bottom of the fuel storage tank is shown. As discussed above with regard to the embodiment shown in FIG. 9, a density magnet 53 is disposed on a density float 51 so as to be in close proximity to probe shaft 14. Note, as compared to previously discussed embodiments, body 59 of density float 51 is configured in a very thin, flat, pancake-like configuration so that density float 51 can respond to a very thin layer of water-ethanol mix on the bottom of the fuel tank. Magnetostrictive density detector 101 shown in FIG. 10 differs only from the density detector shown in FIG. 9 in that it does not include a water level float 40.

Figure 11:
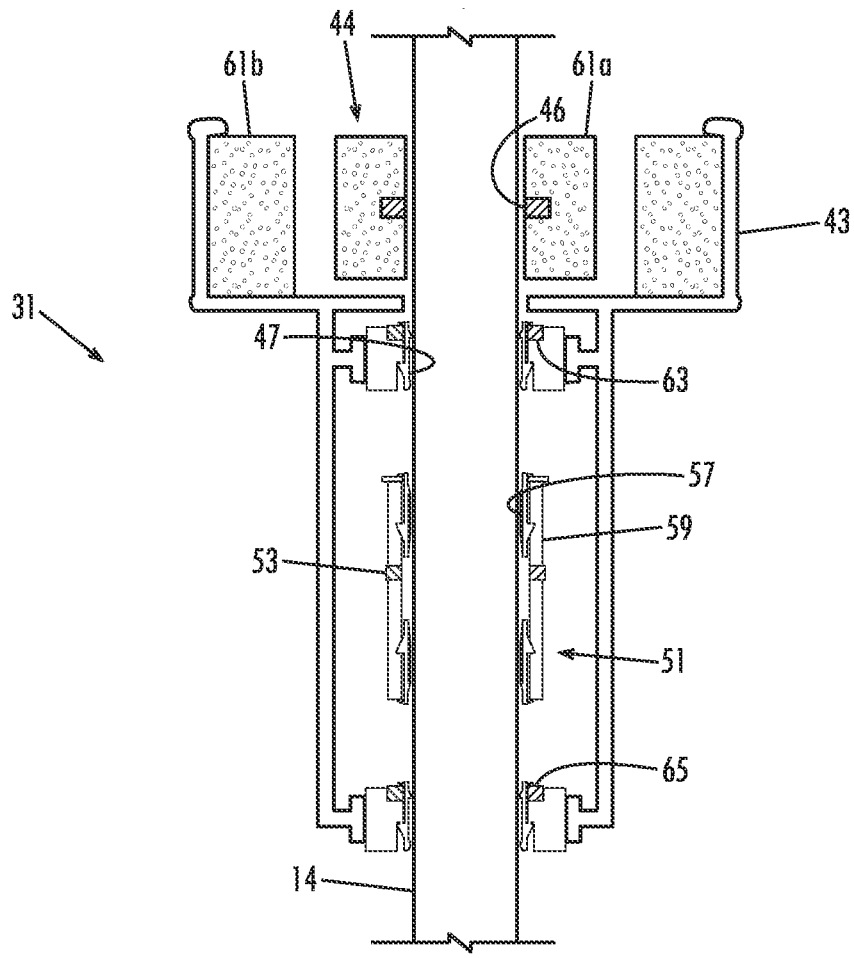
FIG. 11 illustrates a second embodiment of a surface layer magnetostrictive density detector in accordance with the present invention.
Figure 12:
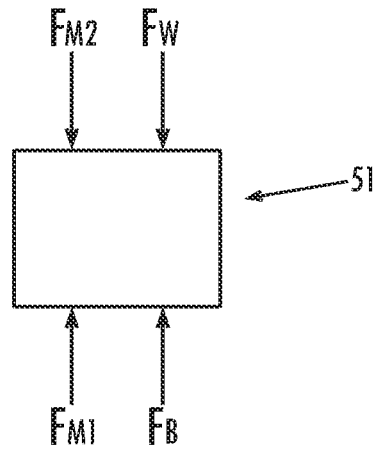
FIG. 12 is a schematic of the surface layer magnetostrictive density detector of FIG. 11, illustrating the principle of magnetic repulsion found in the detector.
Figure 13:
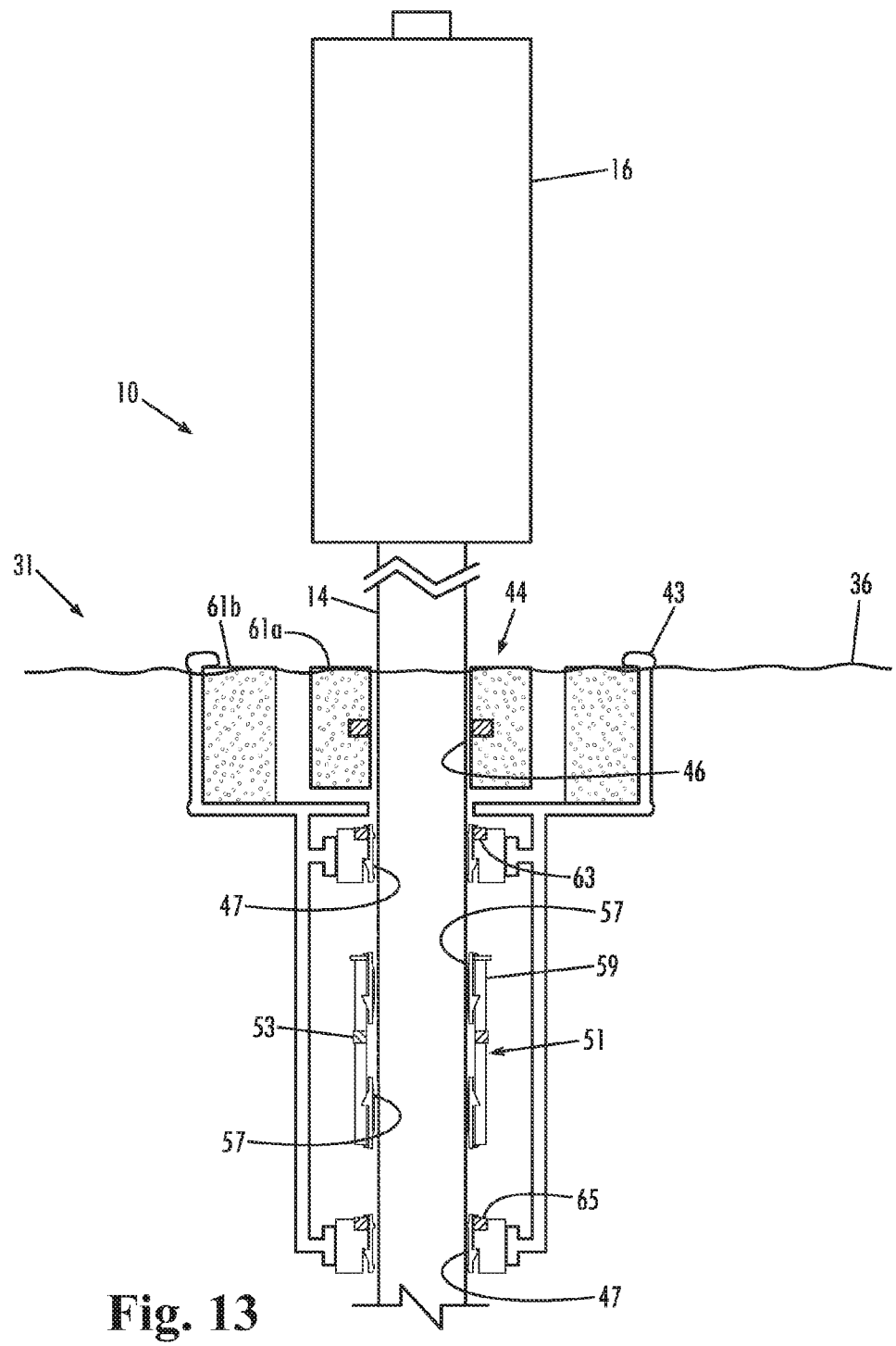
FIG. 13 is a further depiction of the surface layer magnetostrictive density detector of FIG. 11.

Referring now to FIGS. 11 through 13, an alternate embodiment of a magnetostrictive density detector 31 for determining fuel density at the surface layer of the fuel is shown. Magnetostrictive density detector 31 includes a fuel level float 44 and an internal density float 51, and is preferably used in combination with a magnetostrictive probe 10 shown in FIG. 1. Fuel level float 44 includes a fuel level magnet 46 and a body 61a that is independent of body 61b of the density measuring portion. As such, the operation of fuel level float 44 and density float 51 are independent of each other. The density measuring portion of magnetostrictive density detector 31 includes a frame 43, balancing lips 47, body 61b, an upper repulsion magnet 63 and a lower repulsion magnet 65. As shown, upper and lower repulsion magnets 63 and 65 are positioned on opposing portions of frame 43 of magnetostrictive density detector 31 such that internal density float 51 is disposed between repulsion magnets 63 and 65. Balancing lips 47 ensure that magnetostrictive density detector 31 is free to move along probe shaft 14 as fuel level 36 changes within the tank. As well, fuel level float 44 is allowed to float independently of the density measuring portion so that it is also free to move along probe shaft 14 as fuel level 36 changes.

As shown, density float 51 includes a density magnet 53, balancing lips 57 and a body 59. Balancing lips 57 ensure that density float 51 is free to move along probe shaft 14 as fuel level 36 and density of the fuel change.

Figure 14:
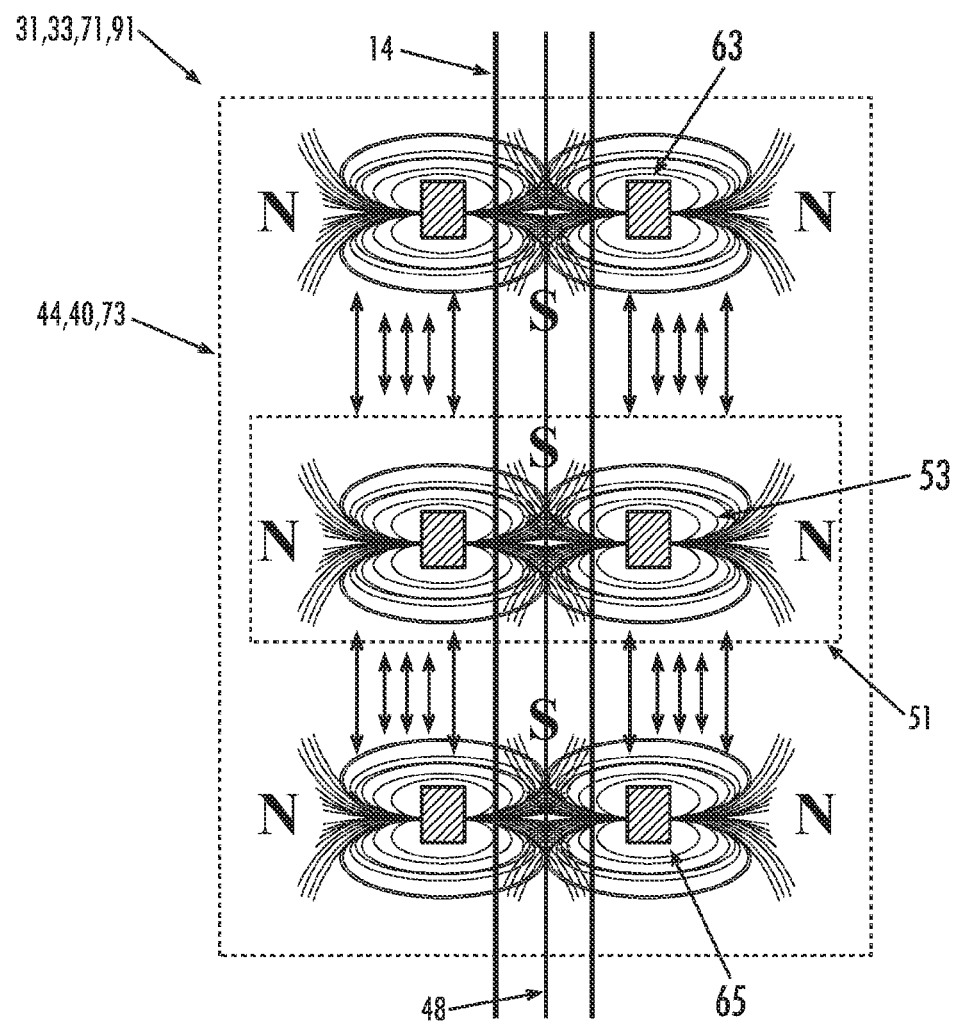
FIG. 14 is a schematic of the magnetostrictive density detector of FIGS. 11, 18 and 19, illustrating the principle of magnetic repulsion found in the detectors.

As best seen in FIG. 14, unlike the previously discussed surface layer magnetostrictive density detectors, density float 51 of the present embodiment is subject to magnetic repulsion forces in both the upward and downward directions due to the fact that density float 51 is positioned between upper and lower repulsion magnets 63 and 65, respectively. Referring additionally to FIG. 12, because both the mass and volume of density float 51 are predetermined fixed values, a force balance can be derived to predict the density of the fuel in which magnetostrictive density detector 31 is submerged. More specifically, the force balance equation is:

$$F_{M1} - F_{M2} + F_B - F_W = 0,$$

wherein, $F_{M1}$ is the magnetic repulsion force produced between lower repulsion magnet 65 and density magnet 53; $F_{M2}$ is the magnetic repulsion force produced between upper repulsion magnet 63 and density magnet 53; $F_B$ is upward force produced by the buoyancy of the density float; and $F_W$ is the downward force produced by the weight of the density float 51. When frame 43 and density float 51 achieve equilibrium in the fuel, the sum of these forces equals 0.

Figure 20:
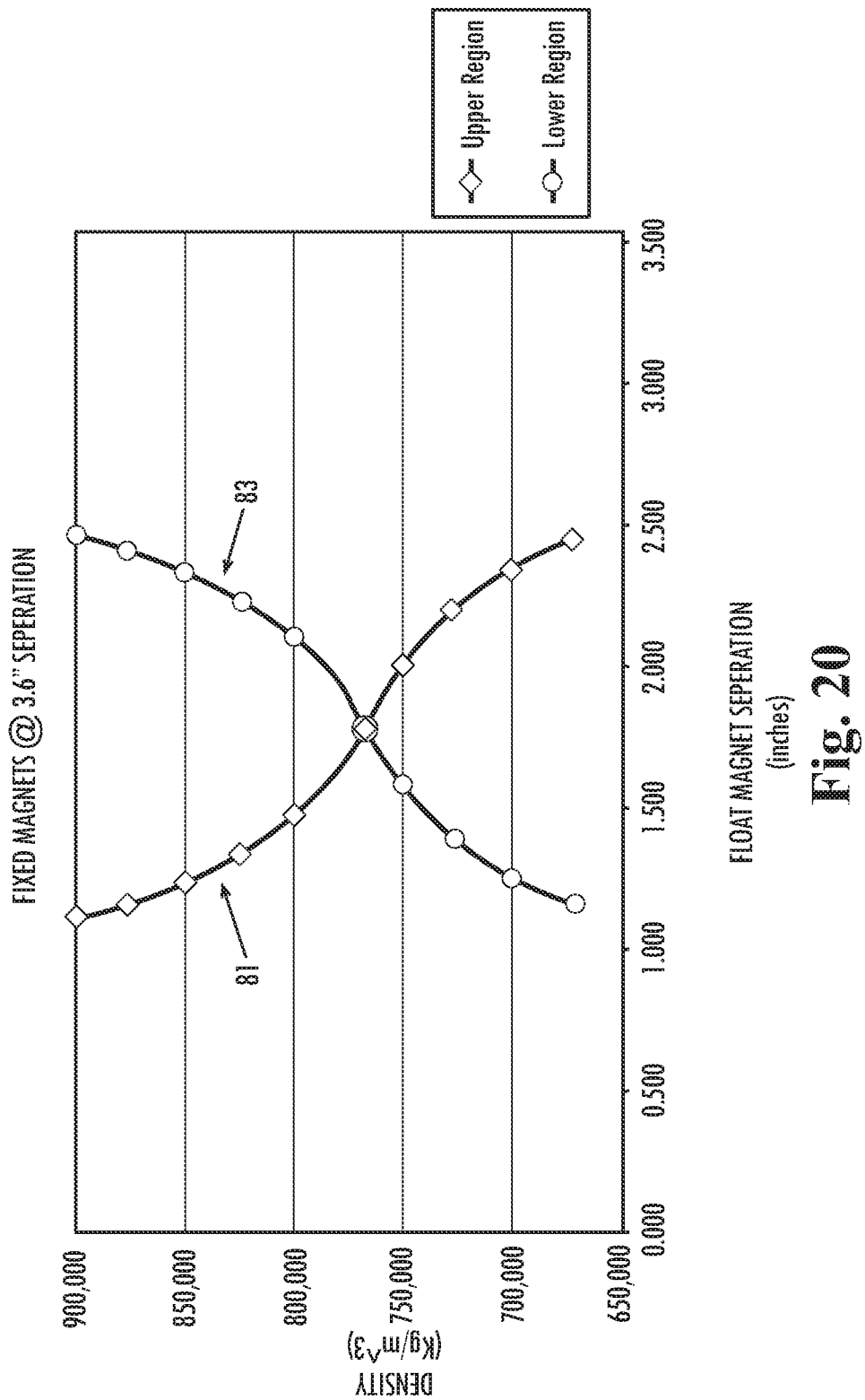
FIG. 20 is a graph illustrating the representative measurements of the distances between the magnets of the density detector of FIG. 11 for varying fuel densities.

Referring now to FIG. 20, an exemplary graph representing the distances between density magnet 53 and upper and lower repulsion magnets 63 and 65, respectively, for varying fuel densities is shown. To determine a fuel density measurement using magnetostrictive density detector 31, the distance between upper repulsion magnet 63 and density magnet 53 (line 81 on the graph) and the distance between lower repulsion magnet 65 and density magnet 53 (line 83 on the graph) is measured. These two distances are measured using the methods and algorithms previously discussed with regard to magnetostrictive probe 10 as shown in FIG. 1. Note, as would be expected, the graph shows that as the fuel density goes up, density float 51 rises relative to fuel level float 44 and the distance from upper repulsion magnet 63 to density magnet 53 decreases as the distance from lower repulsion magnet 65 to density magnet 53 increases. The converse is shown for when fuel density goes down.

The relationship between the displacement of density float 51 and the density of the fuel depends on four factors: the fixed distance between upper repulsion magnet 63 and lower repulsion magnet 65; the material density of density float 51; the volume of density float 51; and the strength of the magnets used. More specifically, the greater the distance between upper repulsion magnet 63 and lower repulsion magnet 65, the greater the resolution that the fuel density measurement will have. However, having too great a distance between upper and lower repulsion magnets 63 and 65 may adversely affect the ability to measure low fuel levels in the tank because, the greater the separation, the greater the length of frame 43. Next, the density of density float 51 determines the center of the range of fuel densities that density detector 31 can measure. Preferably, the density of density float 51 is determined by the average density of the fuel to be measured. Next, the volume of density float 51 is important because the smaller the float, the larger the density range that can be measured. However, a larger density float gives more stable measurements. Lastly, the stronger the magnets that are used in density detector 31, the larger the measurable density range becomes and the more stable the system becomes. By varying these four factors, the magnetostrictive density detector 31 can be designed to cover the desired range of densities for a given fluid. Changes in all four variables due to the temperature changes can be compensated for to achieve accurate density measurements.

Figure 15:
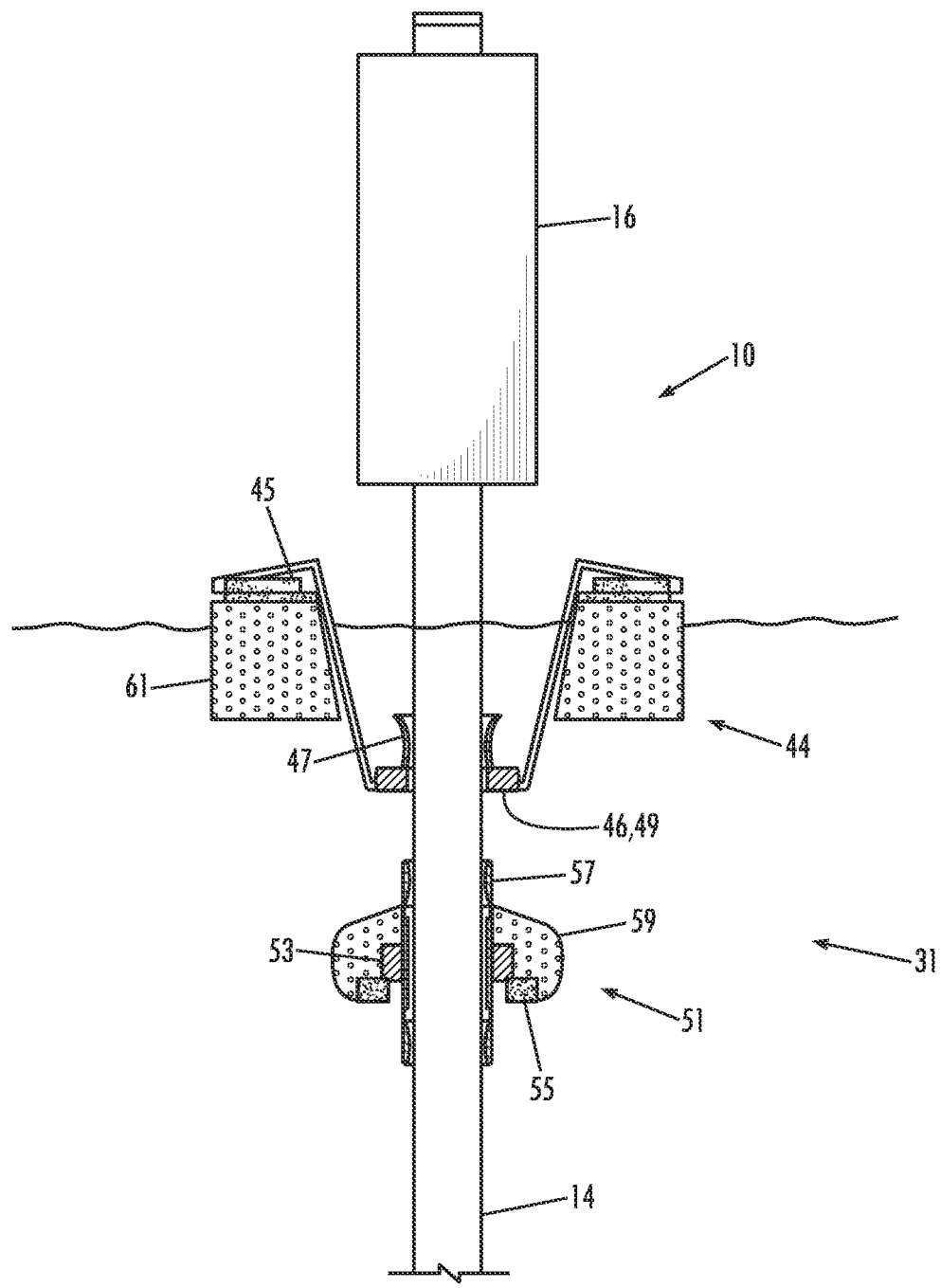
FIG. 15 illustrates a third embodiment of a surface layer magnetostrictive density detector in accordance with the present invention.
Figure 16:
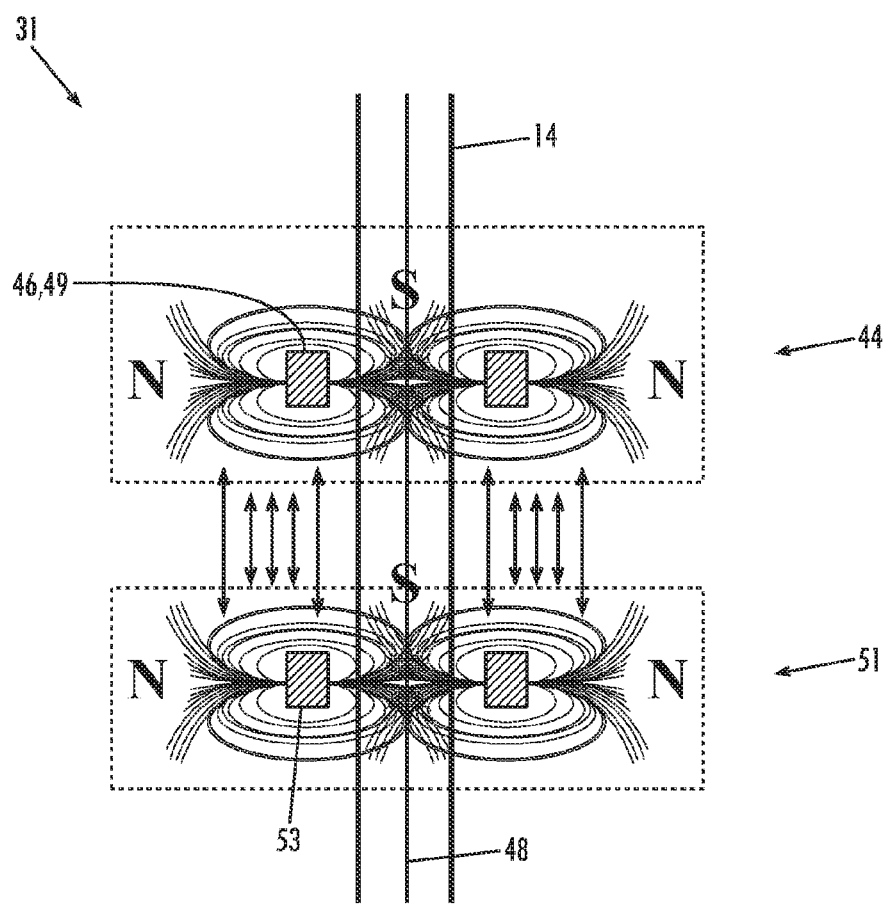
FIG. 16 is a schematic of the surface layer magnetostrictive density detector of FIG. 15, illustrating the principle of magnetic repulsion found in the detector.

Referring now to FIGS. 15 and 16, an alternate embodiment of a magnetostrictive density detector 31 for determining surface layer fuel densities is shown. Magnetostrictive density detector 31 operates similarly to the density detector as shown in FIGS. 2 through 5, with the exception that fuel level magnet 46 also functions as a repulsion magnet 49. More specifically, in contrast to the previously discussed embodiment, fuel level magnet 46 is positioned on a bottom portion of fuel level float 44 such that it is disposed within the fuel. As such, it is in close proximity to density float 51 and therefore generates adequate magnetic repulsion forces with density magnet 53 such that it provides the functionality of the repulsion magnet 49 discussed with regard to the embodiment of density detector 31 shown in FIGS. 2 through 5. Other than this difference, the present embodiment of magnetostrictive density detector 31 functions almost identically to previously discussed embodiment. As such, the previous description of magnetostrictive density detector 31 as shown in FIGS. 2 through 5 applies to the present embodiment, and will not be repeated here.

Figure 17:
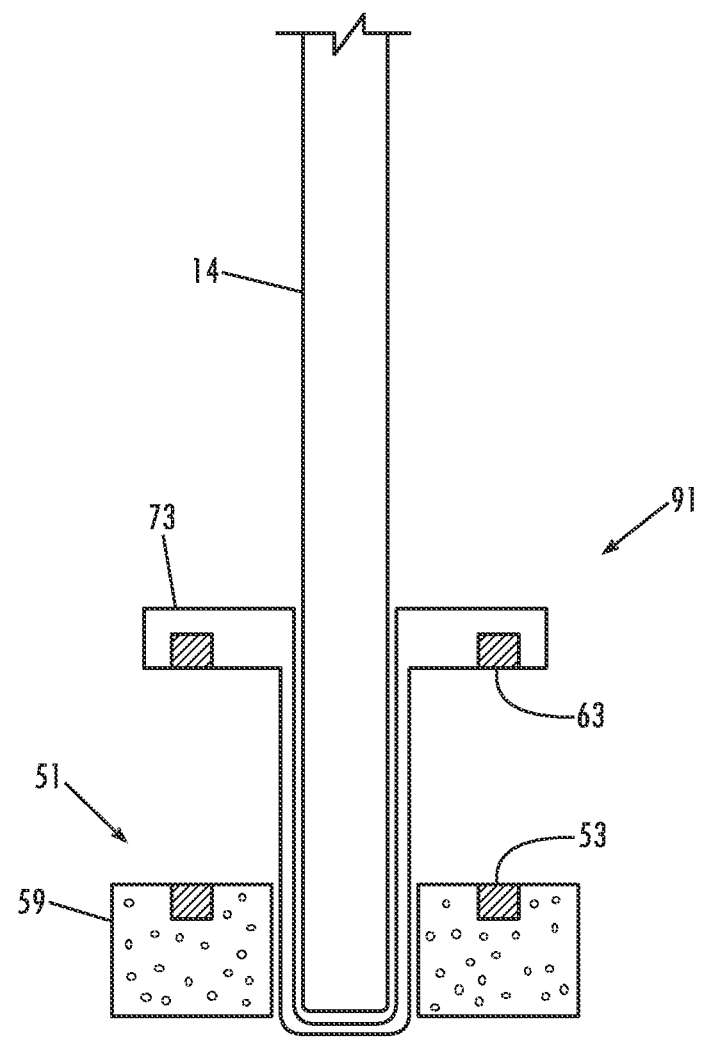
FIG. 17 is a fourth embodiment of a bottom layer magnetostrictive density detector in accordance with the present invention.

Referring now to FIG. 17, an alternate embodiment of a magnetostrictive density detector 91 for detecting fuel density at the bottom of the fuel storage tank is shown. Density detector 91 includes a density float 51 and a boot 73 that is slidably received over the bottom end of probe shaft 14. Boot 73 supports repulsion magnet 63 and is designed such that body 59 can slide axially along its outer surface. Density magnet 53 is imbedded in body 59 and creates the repulsion force to measure the buoyancy of float 51 and determine the density by distance between repulsion magnet 63 and density magnet 53 after equilibrium has been reached, as previously discussed.

Figure 18:
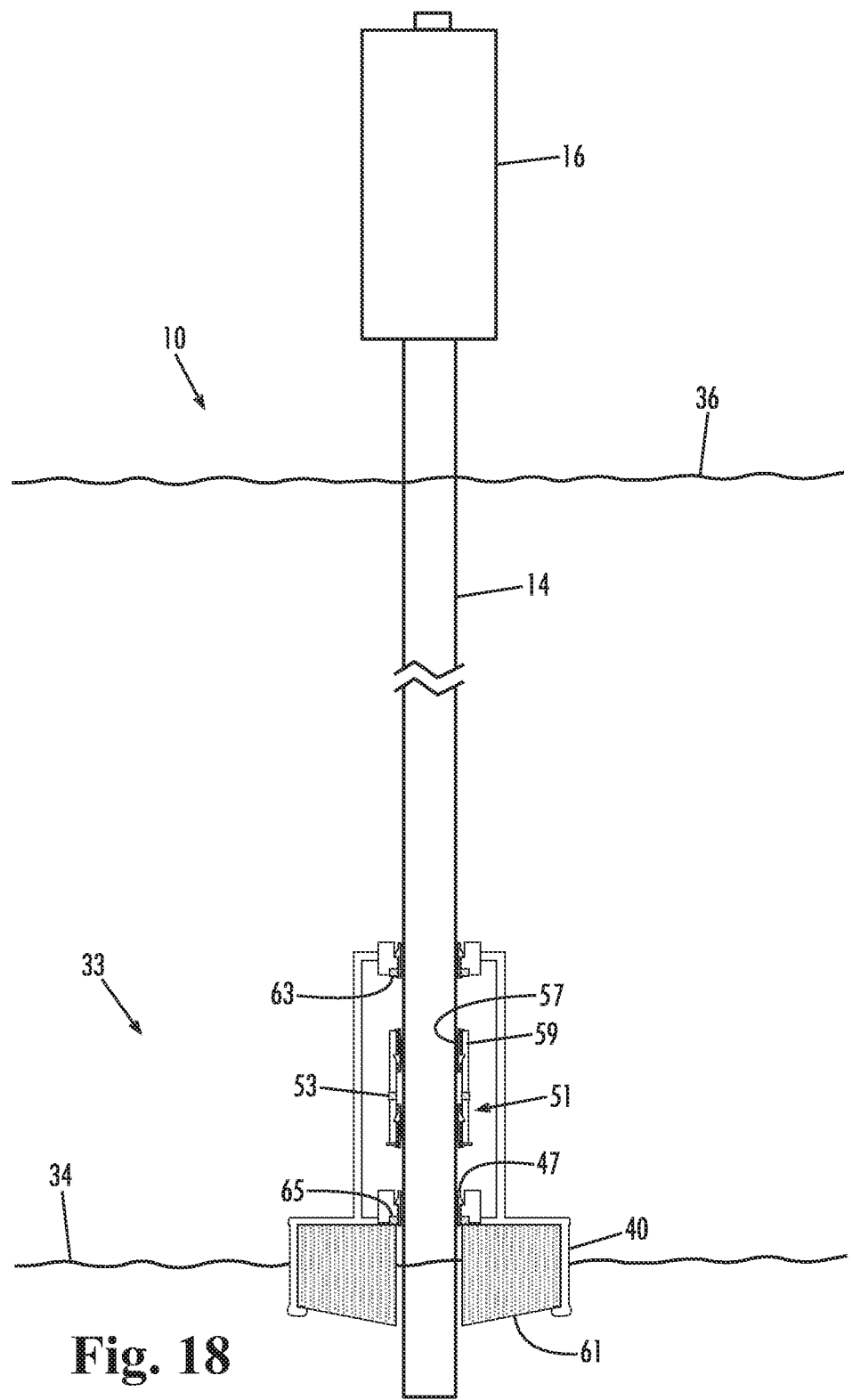
FIG. 18 is a fifth embodiment of a bottom layer magnetostrictive density detector in accordance with the present invention.

Referring now to FIG. 18, a further alternative embodiment of a magnetostrictive density detector 33 for determining fuel density at the water layer of the fuel is shown. Magnetostrictive density detector 33 includes a water level float 40 and an internal density float 51, and is preferably used in combination with a magnetostrictive probe 10 shown in FIG. 1. Water level float 40 includes balancing lips 47, a body 61, an upper repulsion magnet 63 and a lower repulsion magnet 65. As shown, upper and lower repulsion magnets 63 and 65 are positioned on opposing portions of the frame of water level float 40 such that internal density float 51 is disposed between repulsion magnets 63 and 65. Balancing lips 47 ensure that water level float 40 is free to move along probe shaft 14 as water level 34 changes within the tank.

As shown, density float 51 includes a density magnet 53, balancing lips 57 and a body 59. Similarly to balancing lips 47 of water level float 40, balancing lips 57 ensure that density float 51 is free to move along probe shaft 14 as the fuel level and density of the fuel change. The principles of operation of water level density detector 33 are the same as those previously discussed with regard to surface layer density detector 31, as shown in FIG. 11. As such, that discussion is not repeated here.

Figure 19:
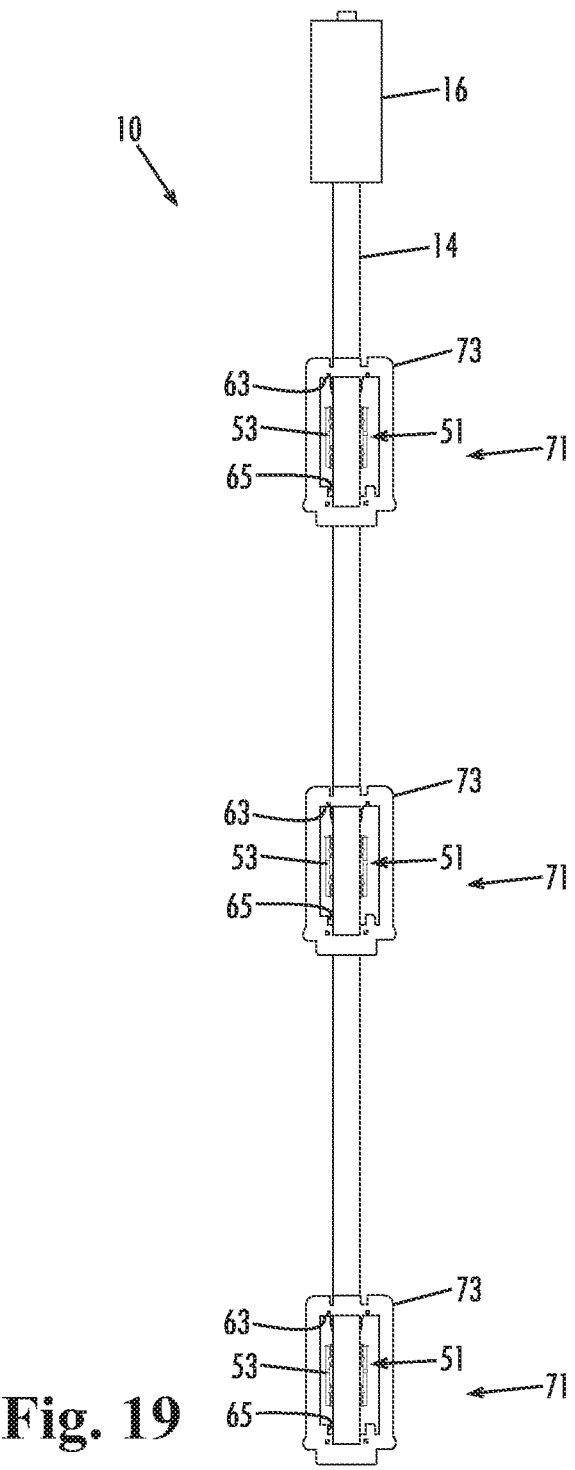
FIG. 19 illustrates an alternate embodiment of magnetostrictive density detector in accordance with the present invention.

Referring now to FIG. 19, a magnetostrictive density detector 71 for determining fuel density at a desired location along a magnetostrictive probe 10 is shown. Magnetostrictive density detector 71 includes a frame 73 and an internal density float 51. Frame 73 is secured to a fixed position on probe shaft 14 of magnetostrictive probe 10 and includes an upper repulsion magnet 63 and a lower repulsion magnet 65. As shown in FIG. 19, upper and lower repulsion magnets 63 and 65 are positioned on opposing portions of frame 73 such that internal density float 51 is disposed between repulsion magnets 63 and 65. As such, density magnet 53 of density float 51 is also positioned between upper and lower repulsion magnets 63 and 65. The primary difference in construction between density detector 71 and previously discussed density detectors 31 and 33, as shown in FIG. 11 and FIG. 18, respectively, is that upper and lower repulsion magnets 63 and 65 are secured to probe shaft 14 in a fixed position that does not vary as the fuel level and water level within the tank vary. As such, the previous description of the operation of density detectors 31 and 33 as shown in FIG. 11 and FIG. 18, respectively, is sufficient to describe the operation of fixed density detector 71, and is therefore not repeated here. This embodiment is desirable because it can be used to detect density across the depth of fuel, thus indicating fuel stratification and other such fuel characteristics. In the illustrated embodiment, for example, a plurality of detectors 71 are fixed at spaced-apart locations along probe shaft 14.

Figure 21:
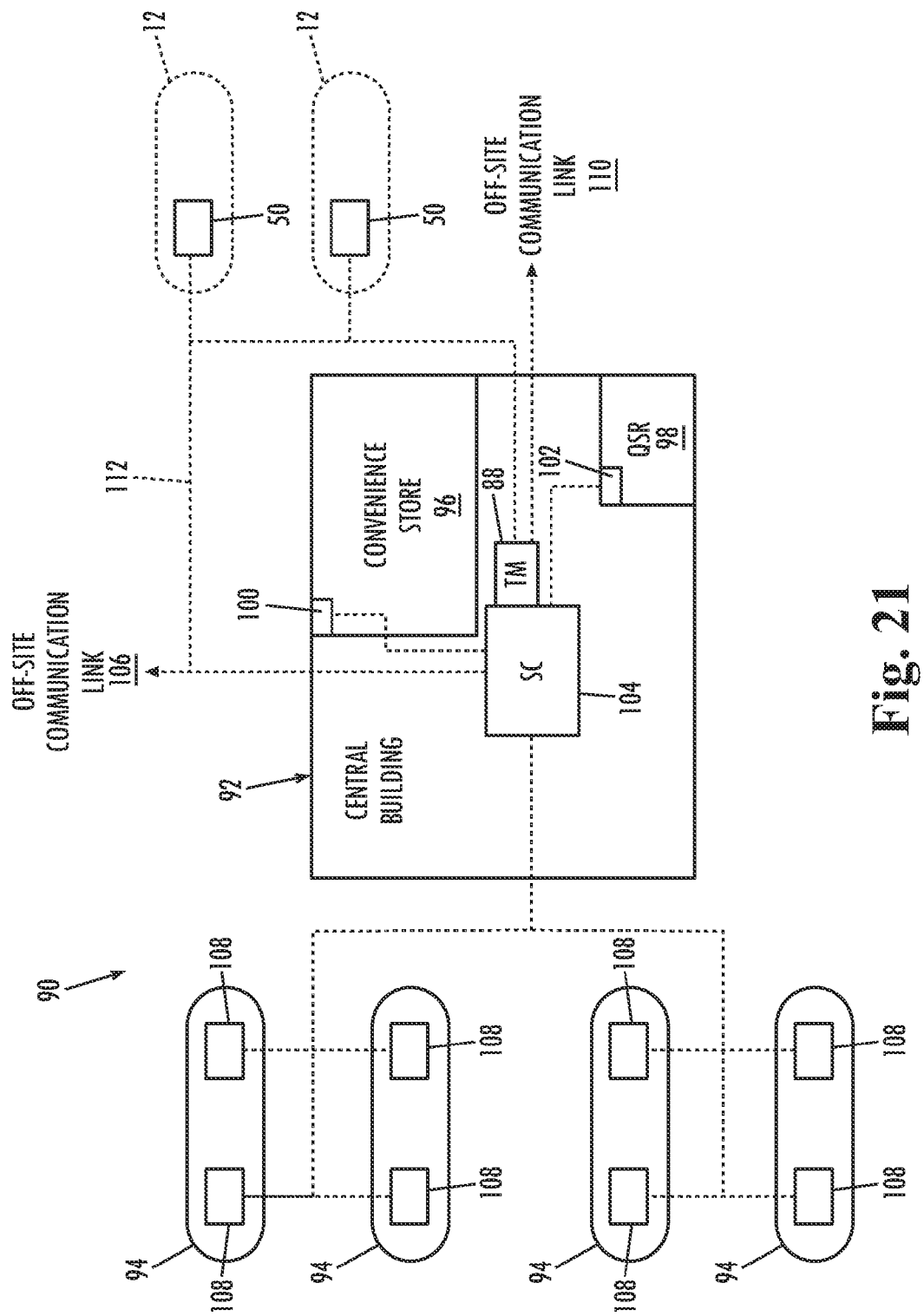
FIG. 21 illustrates a fueling environment incorporating a magnetostrictive density detector in accordance with the present invention.

FIG. 21 illustrates a fueling environment 90 that may incorporate the present invention, and includes the systems and devices that calculate and/or communicate the density of the fuel in the fuel storage tank 12 for the aforementioned purposes. Specifically, the fueling environment 90 may comprise a central building 92 and a plurality of fueling islands 94.

The central building 92 need not be centrally located within the fueling environment 90, but rather is the focus of the fueling environment 90, and may house a convenience store 96 and/or a quick serve restaurant (QSR) 98 therein. Both the convenience store 96 and the quick serve restaurant 98 may include a point of sale 100, 102 respectively. The central building 92 may further house a site controller (SC) 104, which in an exemplary embodiment may be the G-SITE® sold by Gilbarco Inc. of 7300 W. Friendly Avenue, Greensboro, N.C. 27410. The site controller 104 may control the authorization of fueling transactions and other conventional activities as is well understood. The site controller 104 may be incorporated into a point of sale, such as the point of sale 100, if needed or desired. Further, the site controller 104 may have an off-site communication link 106 allowing communication with a remote location for credit/debit card authorization, content provision, reporting purposes, or the like, as needed or desired. The off-site communication link 106 may be routed through the Public Switched Telephone Network (PSTN), the Internet, both, or the like, as needed or desired.

The plurality of fueling islands 94 may have one or more fuel dispensers 108 positioned thereon. The fuel dispensers 108 may be, for example, the ENCORE® dispenser sold by Gilbarco Inc. The fuel dispensers 108 are in electronic communication with the site controller 104 through a LAN or the like.

The fueling environment 90 has one or more fuel storage tanks 12 adapted to hold fuel therein. In a typical installation, fuel storage tanks 12 are positioned underground, and may also be referred to as underground storage tanks. Further, each fuel storage tank 12 has a liquid level probe 50 such as those described herein. The probes 50 report to the tank monitor (TM) 88 associated therewith. Reporting to the tank monitor 88 may be done through a wire-based system, such as an Ethernet LAN, or a wireless system conforming to IEEE standard 802.11g or the like, as needed or desired. The tank monitor 88 may communicate with the fuel dispensers 108 (either through the site controller 104 or directly, as needed or desired) to determine amounts of fuel dispensed, and compare fuel dispensed to current levels of fuel within the fuel storage tanks 12, as needed or desired. In a typical installation, the tank monitor 88 is also positioned in the central building 92, and may be proximate the site controller 104.

The tank monitor 88 may communicate with the site controller 104, and further may have an off-site communication link 110 for leak detection reporting, inventory reporting, or the like. Much like the off-site communication link 106, the off-site communication link 110 may be through the PSTN, the Internet, both, or the like. If the off-site communication link 110 is present, the off-site communication link 106 need not be present, although both links may be present if needed or desired. As used herein, the tank monitor 88 and the site controller 104 are site communicators to the extent that they allow off-site communication and report site data to a remote location.

The present invention may utilize the off-site communication link 110 by forwarding data from the probes 50 to the remote location. This data should preferably be protected from tampering such that the site operator cannot alter the data sent to the remote location through either of the off-site communication links 106 or 110. The data from the probes 50 may be provided to a corporate entity from whom the site operator has a franchise, a governmental monitoring agency, an independent monitoring agency, or the like, as needed or desired. One way to prevent tampering is through an encryption algorithm.

An alternate technique that helps reduce the likelihood of tampering is the use of a dedicated off-site communication link 112, wherein the probes 50 report directly to a location removed from the fueling environment 90. In this manner, the operator of the fueling environment 90 does have not have ready access to the dedicated off-site communication link 112.

For further information on how elements of a fueling environment 90 may interact, reference is made to U.S. Pat. No. 5,956,259, which is hereby incorporated by reference in its entirety. Information about fuel dispensers 108 may be found in U.S. Pat. Nos. 5,734,851 and 6,052,629, which are hereby incorporated by reference in their entireties. For more information about tank monitors 88 and their operation, reference is made to U.S. Pat. Nos. 5,423,457; 5,400,253; 5,319,545; and 4,977,528, which are hereby incorporated by reference in their entireties.

Those skilled in the art will recognize improvements and modifications to the preferred embodiments of the present invention. For example, while magnetostrictive density detectors have been used in the above description, one skilled in the art will appreciate that any other suitable density detectors may also be used. All such improvements and modifications are considered within the scope of the concepts disclosed herein and the claims that follow.

What is claimed is:

1. A fluid level probe for use in a tank containing a first fluid, comprising:
   a probe shaft including a top end and a bottom end;
   a first float carrying a first magnet, the first float being slidably disposed for movement along the probe shaft within the first fluid;
   a second float carrying a first magnet, the second float being slidably disposed for movement along the probe shaft beneath the first float and adapted to float within the first fluid such that there is magnetic repulsion between the first magnet of the first float and the first magnet of the second float;
   a frame carrying a first magnet;
   a third float carrying a first magnet, the third float being slidably disposed for movement along the probe shaft relative to the first magnet of the frame and adapted to float within the first fluid such that there is magnetic repulsion between the first magnet of the third float and the first magnet of the frame;
   electronics operative to determine a first distance between the first magnet of the first float and the first magnet of the second float, determine a second distance between the first magnet of the frame and the first magnet of the third float, utilize the first distance to determine a first density of the first fluid adjacent the top surface of the first fluid, utilize the second distance to determine a second density of the first fluid adjacent a bottom of the tank, and determine whether phase separation has occurred within the first fluid by comparing the first density and the second density of the first fluid.

2. The fluid level probe of claim 1, wherein the first fluid further comprises an upper layer of fluid, a lower layer of fluid and a top surface of the lower layer of fluid comprises a phase separation boundary, and the electronics are further operative to utilize the first density of the first fluid and the second density of the first fluid to determine a height of the phase separation boundary relative to a bottom of the tank.

3. The fluid level probe of claim 1, wherein the frame is in a fixed position relative to the probe shaft.

4. The fluid level probe of claim 1, wherein the first fluid further comprises an upper layer of fluid and a lower layer of fluid, separated at a phase separation boundary, and the electronics are further operative to utilize the first density of the first fluid and the second density of the first fluid to determine a first volume of the lower layer of fluid.

5. The fluid level probe of claim 4, wherein the electronics are further operative to utilize the first volume of the lower layer of fluid to determine a height of the phase separation boundary relative to a bottom of the tank.

6. The fluid level probe of claim 1, wherein the first float is adapted to float at a top surface of the first fluid.

7. The fluid level probe of claim 6, further comprising a reference magnet disposed at a predetermined location along the probe shaft and a magnetostrictive wire extending along the length of the probe shaft.

8. The fluid level probe of claim 6, wherein a position of the first magnet of the first float relative to the probe shaft is used to determine a position of the top surface of the first fluid relative to the probe shaft.

9. The fluid level probe of claim 6, wherein the first fluid is a fuel and the top surface of the fuel comprises an air-fuel interface.

10. The fluid level probe of claim 6, wherein the first fluid is a fuel including anhydrous ethanol.

11. The fluid level probe of claim 6, further comprising:
    a fourth float including the frame, the fourth float being slidably disposed for movement along the probe shaft and adapted to float at a top surface of a second fluid within the tank,
    wherein the second fluid is more dense than the fuel.

12. The fluid level probe of claim 11, wherein the second fluid comprises water and the top surface of the water comprises a fuel-water interface.

* * * * *